(12) United States Patent
Gunther

(10) Patent No.: US 10,786,265 B2
(45) Date of Patent: *Sep. 29, 2020

(54) METHODS FOR LESS INVASIVE GLENOID REPLACEMENT

(71) Applicant: Shoulder Innovations, Inc., Holland, MI (US)

(72) Inventor: Stephen B. Gunther, Charlottesville, VA (US)

(73) Assignee: Shoulder Innovations, Inc., Holland, MI (US)

( * ) Notice: Subject to any disclaimer, the term of this patent is extended or adjusted under 35 U.S.C. 154(b) by 141 days.

This patent is subject to a terminal disclaimer.

(21) Appl. No.: 15/640,039

(22) Filed: Jun. 30, 2017

(65) Prior Publication Data

US 2017/0360456 A1 Dec. 21, 2017

Related U.S. Application Data

(63) Continuation of application No. 13/776,405, filed on Feb. 25, 2013, now Pat. No. 9,693,784, which is a
(Continued)

(51) Int. Cl.
*A61F 2/40* (2006.01)
*A61B 17/16* (2006.01)
(Continued)

(52) U.S. Cl.
CPC .......... *A61B 17/1684* (2013.01); *A61B 17/15* (2013.01); *A61F 2/4059* (2013.01); *A61F 2/4081* (2013.01); *A61B 17/00234* (2013.01); *A61B 17/1659* (2013.01); *A61B 17/86* (2013.01); *A61F 2/30767* (2013.01); *A61F 2/30771* (2013.01); *A61F 2/40* (2013.01); *A61F 2/4684* (2013.01); *A61F 2002/3069* (2013.01); *A61F 2002/30112* (2013.01); *A61F 2002/30113* (2013.01); *A61F 2002/30118* (2013.01); *A61F 2002/30125* (2013.01);
(Continued)

(58) Field of Classification Search
CPC .................................................... A61F 2/4081
See application file for complete search history.

(56) References Cited

U.S. PATENT DOCUMENTS 2,781,758 A 2/1957 Jacques
3,979,778 A 9/1976 Stroot
(Continued)

FOREIGN PATENT DOCUMENTS

DE 10164328 A1 7/2003
EP 0299889 A2 1/1989
(Continued)

OTHER PUBLICATIONS

Biomet, "Absolute™ Bi-Polar." 2001 in 2 pages.
(Continued)

*Primary Examiner* — David H Willse
*Assistant Examiner* — Javier G Blanco
(74) *Attorney, Agent, or Firm* — Knobbe, Martens, Olson & Bear LLP

(57) ABSTRACT

The invention features a glenoid (shoulder socket) implant prosthesis, a humeral implant prosthesis, devices for implanting glenoid and humeral implant prostheses, and less invasive methods of their use for the treatment of an injured or damaged shoulder.

19 Claims, 26 Drawing Sheets

Related U.S. Application Data continuation of application No. 12/561,528, filed on Sep. 17, 2009, now abandoned, which is a continuation of application No. 11/066,978, filed on Feb. 25, 2005, now Pat. No. 8,007,538.

(51) Int. Cl.

| | | |
|---|---|---|
| *A61B 17/15* | (2006.01) | |
| *A61B 17/00* | (2006.01) | |
| *A61B 17/86* | (2006.01) | |
| *A61F 2/30* | (2006.01) | |
| *A61F 2/46* | (2006.01) | |

(52) U.S. Cl.
CPC .............. *A61F 2002/30153* (2013.01); *A61F 2002/30332* (2013.01); *A61F 2002/30574* (2013.01); *A61F 2002/30606* (2013.01); *A61F 2002/30609* (2013.01); *A61F 2002/30822* (2013.01); *A61F 2002/30827* (2013.01); *A61F 2002/30878* (2013.01); *A61F 2002/30884* (2013.01); *A61F 2002/4033* (2013.01); *A61F 2002/4051* (2013.01); *A61F 2002/4062* (2013.01); *A61F 2002/4631* (2013.01); *A61F 2002/4635* (2013.01); *A61F 2220/0033* (2013.01); *A61F 2230/0004* (2013.01); *A61F 2230/0006* (2013.01); *A61F 2230/0008* (2013.01); *A61F 2230/0019* (2013.01); *A61F 2310/00011* (2013.01); *A61F 2310/00179* (2013.01)

(56) References Cited

U.S. PATENT DOCUMENTS

| | | |
|---|---|---|
| 4,003,095 A | 1/1977 | Gristina |
| 4,045,826 A | 9/1977 | Stroot |
| 4,206,517 A | 6/1980 | Pappas et al. |
| 4,261,062 A | 4/1981 | Amstutz et al. |
| 4,404,693 A | 9/1983 | Zweymuller |
| 4,550,450 A | 11/1985 | Kinnett |
| 4,865,605 A | 9/1989 | Dines et al. |
| 4,964,865 A | 10/1990 | Burkhead et al. |
| 4,986,833 A | 1/1991 | Worland |
| 4,990,161 A | 2/1991 | Kampner |
| 5,030,219 A | 7/1991 | Matsen, III et al. |
| 5,032,132 A | 7/1991 | Matsen, III et al. |
| 5,080,673 A | 1/1992 | Burkhead et al. |
| 5,108,440 A | 4/1992 | Grundei |
| 5,282,865 A | 2/1994 | Dong |
| 5,314,479 A | 5/1994 | Rockwood, Jr. et al. |
| 5,314,489 A | 5/1994 | Hoffman et al. |
| 5,344,458 A | 9/1994 | Bonutti |
| 5,358,525 A | 10/1994 | Fox et al. |
| 5,370,694 A | 12/1994 | Davidson |
| 5,437,677 A | 8/1995 | Shearer et al. |
| 5,462,563 A | 10/1995 | Shearer et al. |
| 5,489,309 A | 2/1996 | Lackey et al. |
| 5,489,310 A | 2/1996 | Mikhail |
| 5,507,819 A | 4/1996 | Wolf |
| 5,514,184 A | 5/1996 | Doi |
| 5,549,683 A | 8/1996 | Bonutti |
| 5,593,448 A | 1/1997 | Dong |
| 5,755,811 A | 5/1998 | Tanamal et al. |
| 5,769,856 A | 6/1998 | Dong et al. |
| 5,800,551 A | 9/1998 | Williamson et al. |
| 5,928,285 A | 7/1999 | Bigliani et al. |
| 6,228,119 B1 | 5/2001 | Ondria et al. |
| 6,231,913 B1 | 5/2001 | Schwimmer et al. |
| 6,290,726 B1 | 9/2001 | Pope et al. |
| 6,334,874 B1 | 1/2002 | Tornier et al. |
| 6,364,910 B1 | 4/2002 | Shultz et al. |
| 6,368,353 B1 | 4/2002 | Arcand |
| 6,379,386 B1 | 4/2002 | Resch et al. |
| 6,458,136 B1 | 10/2002 | Allard et al. |
| 6,514,287 B2 | 2/2003 | Ondria et al. |
| 6,520,964 B2 | 2/2003 | Tallarida et al. |
| 6,589,281 B2 | 7/2003 | Hyde, Jr. |
| 6,610,067 B2 | 8/2003 | Tallarida et al. |
| 6,620,197 B2 | 9/2003 | Maroney |
| 6,673,115 B2 | 1/2004 | Resch et al. |
| 6,679,916 B1 | 1/2004 | Frankle et al. |
| 6,679,917 B2 | 1/2004 | Ek |
| 6,699,289 B2 | 3/2004 | Iannotti et al. |
| 6,712,823 B2 | 3/2004 | Grusin et al. |
| 6,761,740 B2 | 7/2004 | Tornier |
| 6,783,549 B1 | 8/2004 | Stone et al. |
| 6,875,234 B2 | 4/2005 | Lipman et al. |
| 7,011,686 B2 | 3/2006 | Ball et al. |
| 7,238,208 B2 | 7/2007 | Camino et al. |
| 7,294,149 B2 | 11/2007 | Hozack et al. |
| 7,329,284 B2 | 2/2008 | Maroney et al. |
| 7,465,319 B2 | 12/2008 | Tornier |
| 7,517,364 B2 | 4/2009 | Long et al. |
| 7,749,278 B2 | 7/2010 | Frederick et al. |
| 7,776,098 B2 | 8/2010 | Murphy |
| 7,892,287 B2 | 2/2011 | Deffenbaugh |
| 7,922,769 B2 | 4/2011 | Deffenbaugh et al. |
| 8,007,538 B2 | 8/2011 | Gunther |
| 8,038,719 B2 | 10/2011 | Gunther |
| 8,048,161 B2 | 11/2011 | Guederian et al. |
| 8,048,167 B2 | 11/2011 | Dietz et al. |
| 8,529,629 B2 | 9/2013 | Angibaud et al. |
| 8,778,028 B2 | 7/2014 | Gunther et al. |
| 9,381,086 B2 | 7/2016 | Ries et al. |
| 9,610,166 B2 | 4/2017 | Gunther et al. |
| 9,693,784 B2 | 7/2017 | Gunther |
| 2001/0011192 A1 | 8/2001 | Ondria et al. |
| 2001/0037153 A1 | 11/2001 | Rockwood, Jr. et al. |
| 2001/0047210 A1 | 11/2001 | Wolf |
| 2002/0082702 A1 | 6/2002 | Resch et al. |
| 2002/0087213 A1 | 7/2002 | Bertram, III |
| 2002/0095214 A1 | 7/2002 | Hyde, Jr. |
| 2002/0111689 A1 | 8/2002 | Hyde, Jr. et al. |
| 2002/0138148 A1 | 9/2002 | Hyde, Jr. et al. |
| 2003/0100952 A1 | 5/2003 | Rockwood, Jr. et al. |
| 2003/0114933 A1 | 6/2003 | Bouttens et al. |
| 2003/0125809 A1 | 7/2003 | Iannotti et al. |
| 2003/0144738 A1 | 7/2003 | Rogalski |
| 2003/0158605 A1 | 8/2003 | Tournier |
| 2003/0163202 A1 | 8/2003 | Lakin |
| 2003/0236572 A1 | 12/2003 | Bertram, III |
| 2004/0002766 A1 | 1/2004 | Hunter et al. |
| 2004/0039449 A1 | 2/2004 | Tournier |
| 2004/0039451 A1 | 2/2004 | Southworth |
| 2004/0059424 A1 | 3/2004 | Guederian et al. |
| 2004/0064187 A1 | 4/2004 | Ball et al. |
| 2004/0064189 A1 | 4/2004 | Maroney et al. |
| 2004/0064190 A1 | 4/2004 | Ball et al. |
| 2004/0107002 A1 | 6/2004 | Katsuya |
| 2004/0122519 A1 | 6/2004 | Wiley et al. |
| 2004/0122520 A1 | 6/2004 | Lipman et al. |
| 2004/0167629 A1 | 8/2004 | Geremakis et al. |
| 2004/0167630 A1 | 8/2004 | Rolston |
| 2004/0193168 A1 | 9/2004 | Long et al. |
| 2004/0193275 A1 | 9/2004 | Long et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0230311 A1 | 11/2004 | Cyprien et al. |
| 2004/0260398 A1 | 12/2004 | Kelman |
| 2005/0043805 A1 | 2/2005 | Chudik |
| 2005/0049709 A1 | 3/2005 | Tornier |
| 2005/0065612 A1 | 3/2005 | Winslow |
| 2005/0107882 A1 | 5/2005 | Stone et al. |
| 2005/0119531 A1 | 6/2005 | Sharratt |
| 2006/0069443 A1 | 3/2006 | Deffenbaugh et al. |
| 2006/0069444 A1 | 3/2006 | Deffenbaugh et al. |
| 2006/0069445 A1 | 3/2006 | Ondrla et al. |
| 2007/0038302 A1 | 2/2007 | Shultz et al. |
| 2007/0050042 A1 | 3/2007 | Dietz et al. |
| 2007/0055380 A1 | 3/2007 | Berelsman et al. |

(56) References Cited

U.S. PATENT DOCUMENTS

| | | |
|---|---|---|
| 2007/0112433 A1 | 5/2007 | Frederick et al. |
| 2007/0225817 A1 | 9/2007 | Ruebelt et al. |
| 2007/0225818 A1 | 9/2007 | Reubelt et al. |
| 2008/0021564 A1 | 1/2008 | Gunther |
| 2008/0234820 A1 | 9/2008 | Felt et al. |
| 2009/0125113 A1 | 5/2009 | Guederian et al. |
| 2009/0228112 A1 | 9/2009 | Clark et al. |
| 2010/0087876 A1 | 4/2010 | Gunther |
| 2010/0087877 A1 | 4/2010 | Gunther |
| 2010/0114326 A1 | 5/2010 | Winslow et al. |
| 2010/0274360 A1 | 10/2010 | Gunther |
| 2011/0144758 A1 | 6/2011 | Deffenbaugh |
| 2011/0276144 A1 | 11/2011 | Wirth et al. |
| 2011/0313533 A1 | 12/2011 | Gunther |
| 2013/0060346 A1 | 3/2013 | Collins |
| 2013/0166033 A1 | 6/2013 | Gunther |
| 2015/0105861 A1 | 4/2015 | Gunther et al. |
| 2017/0202674 A1 | 7/2017 | Gunther et al. |

FOREIGN PATENT DOCUMENTS

| | | |
|---|---|---|
| EP | 0339530 A2 | 11/1989 |
| EP | 1952788 A1 | 8/2008 |
| EP | 2083759 B1 | 9/2015 |
| FR | 2248820 A1 | 5/1975 |
| FR | 2567019 A1 | 1/1986 |
| FR | 2695313 A1 | 3/1994 |
| WO | WO 2009/071940 A1 | 6/2009 |

OTHER PUBLICATIONS

Biomet, "Copeland™ Humeral Resurfacing Head, Interlok®/HA Coated Implant Information," 2003 in 1 page.

Biomet, "Copeland™ Humeral Resurfacing Head," 2001 in 12 pages.

Biomet, "Copeland™ Humeral Resurfacing Head, Macrobond™ Implant Information," 2003 in 1 page Biomet, "Copeland™ Humeral Resurfacing Head, Surgical Technique," 2003 in 2 pages.

Boileau et al., "The Three-Dimensional Geometry of the Proximal Humerus. Implications for Surgical Technique and Prosthetic Design," J. Bone Joint Surg. Br. 79: 857-865, 1997.

Braun, et al., Modular Short-stem Prosthesis in Total Hip Arthroplasty: Implant Positioning and the Influence of Naviation, ORTHO SuperSite (Oct. 2007) in 8 pages.

Clavert et al. Glenoid resurfacing: what are the limits to asymmetric reaming for posterior erosion? J. Shoulder and Elbow Surg. Nov./Dec. 2007: 843-848.

Dalla Pria, Paolo. Slide presentation, entitled "Shoulder Prosthesis Design and Evolution", to the Naples International Shoulder Congress in Italy (2000) in 55 pages.

DePuy, "Global C.A.P., Surgical Technique Resurfacing Humeral Head Implant," 2004 in 23 pages.

Inset Mini-glenoid Brochure, Ascension Orthopedics, 2011, 4 pages.

Karduna et al. Glenhumeral Joint Translations before and after Total Shoulder Arthroplasty. J. Bone and Joint Surg. 79(8) (1997): 1166-1174.

Redacted letter from a third party dated Aug. 24, 2012 in 2 pages.

Levy et al., "Cementless Surface Replacement Arthroplasty of the Should. 5- to 10-year Results with the Copeland Mark-2 Prosthesis," J. Bone Joint Surg. Br. 83: 213-221, 2001.

Lima-Lto Medical Systems Glenoidi/Glenoids catalogue (2001) in 1 page.

Lima-Lto Miniglenoide Cementata document 7560.50.030 (1999) in 1 page.

Panisello, et al., Bone remodelling after total hip arthroplasty using an uncemented anatomic femoral stem: a three-year prospective study using bone densitometry, J Ortho Surg 14(1):32-37 (2006).

Ross, Mark and Duke, Phillip, "Early Experience in the Use of a New Glenoid Resurfacing Technique" Glenoid Presentation, SESA Nov. 4, 2006, Session 4/0800-0930 p. 93 in 1 page.

Search Report and Written Opinion in PCT/US2006/006330 dated Jan. 24, 2008 in 10 pages.

Office Action in Australian Application No. 2011224694 dated Sep. 2, 2013 in 2 pages.

Office Action in European Application No. 11753831.4 dated Nov. 16, 2016 in 3 pages.

Titan(TM) Modular Shoulder System Brochure, 2011, available at http://www.ascensionortho.com/Assets/PDF/TitanModular/TITANModularShoulder_Brochure-revD.pdf (2 pages).

Tournier et al., Enhancement of Glenoid Prosthesis Anchorage using Burying Technique. Techniques in Shoulder & Elbow Surgery 9(1)(2008): 35-42.

Wang et al., Biomechanical Evaluation of a Novel Glenoid Design in Total Shoulder Arthroplasty. J. Shoulder & Elbow Surgery (2005) 15: 129S-140S.

Statement of Grounds and Particulars of Opposition for Australian Patent Application No. 2006218936 dated Oct. 5, 2012 in 8 pages.

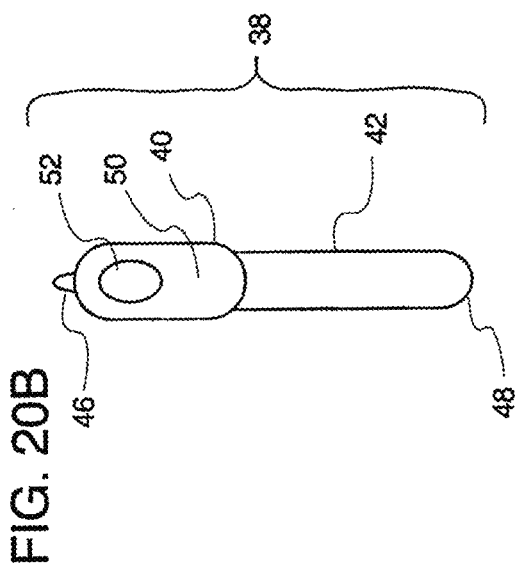
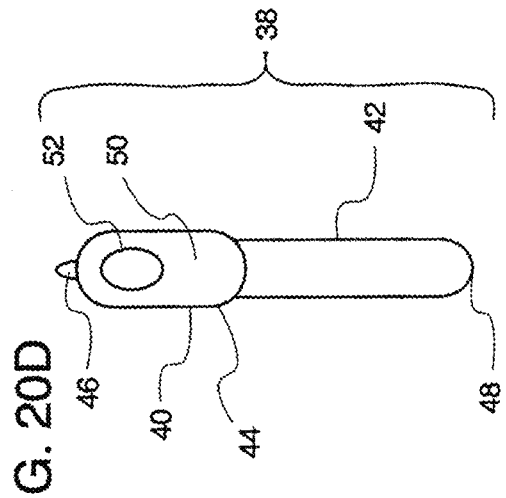
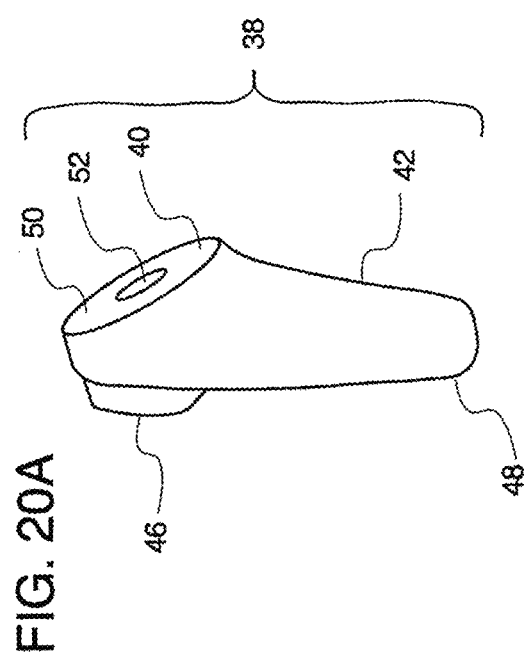
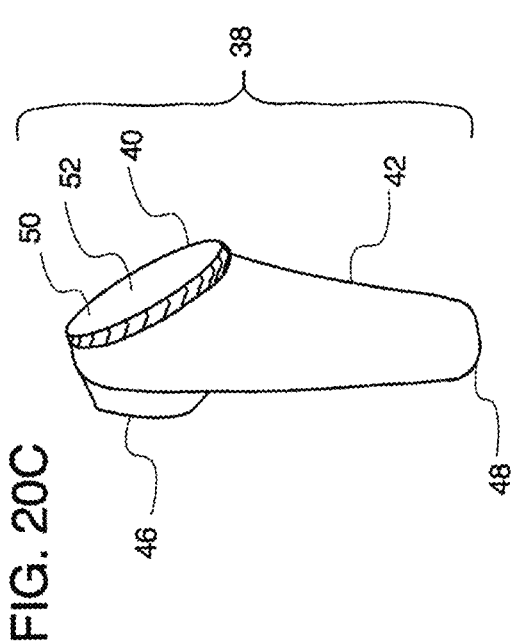

METHODS FOR LESS INVASIVE GLENOID REPLACEMENT

CROSS-REFERENCE TO RELATED APPLICATIONS

This application claims the benefit under 35 U.S.C. § 120 as a continuation application of U.S. patent application Ser. No. 13/776,405 filed on Feb. 25, 2013 and currently pending, which in turn is a continuation of U.S. patent application Ser. No. 12/561,528 filed on Sep. 17, 2009 now abandoned, which in turn is a continuation application of U.S. patent application Ser. No. 11/066,978 filed on Feb. 25, 2005, issued on Aug. 30, 2011 as U.S. Pat. No. 8,007,538. Each of the aforementioned priority applications are incorporated by reference in their entireties herein and made a part of the present specification.

FIELD OF THE INVENTION

The present invention relates to the field of glenoid surface replacement.

BACKGROUND OF THE INVENTION

The invention provides a glenoid shoulder implant, a humeral implant, and devices for preparing the glenoid and humeral head for joint replacement.

Shoulder replacement surgery is currently used to treat patients suffering from disabling pain due to worn or damaged shoulder joints, which can be caused by, e.g., arthritis or injury. The humeral implants currently in use are typically made from metal, and the implants are affixed to the bone using bone cement (e.g., polymethylmethacrylate) or by press fitting the implant into the bone using a roughened outer surface coating on the metal for bony integration. Most glenoid (shoulder socket) implants are made completely from polyethylene and affixed to the cortical bone using bone cement. Some glenoid implants have a metal base plate with a polyethylene insert. Current glenoid implants are made to sit on the surface of a reamed glenoid, which is prepared by removing any remaining cartilage and flattening the bony surface. These implants use either a keel or multiple elongated pegs on the back of the prosthetic glenoid implant to secure the glenoid implant inside the glenoid vault.

Keeled and pegged glenoid implants suffer from several disadvantages, which limit their lifespan once implanted and reduce the number of indications for which they can be used when the age of the patient is a factor. For example, the glenoid implants can loosen due to poor fixation within the bone, and they are prone to wear and fatigue failure of the polyethylene due to adhesion, abrasion, and shear stress. Because of these deficiencies, surgeons hesitate to perform glenoid replacement surgery on young or middle aged patients with glenoid articular cartilage injuries or damage due to early arthritis for fear that the implant may not last more than 10-15 years in the body, thus subjecting the patient to the possibility of two or more surgeries during the lifetime of the patient to preserve the function and pain-free state of the joint. Finally, current glenoid implants with a long keel or pegs are sometimes contraindicated in patients with significant glenoid bone loss. As arthritis progresses, the humeral head can wear medially and destroy the foundation of glenoid bone. In these cases, the glenoid vault can be significantly reduced in volume and depth. Thus, a typical keel or peg design can broach the glenoid vault and injure the suprascapular nerve along the suprascapular notch or spinoglenoid notch with resultant denervation injury to the rotator cuff muscles. Broaching through the glenoid vault can also fracture the body of the scapula and cause early implant loosening.

There are also several disadvantages associated with current glenoid replacement surgical techniques. Current techniques require extensive shoulder exposure with capsular releases in order to fully expose the glenoid surface circumferentially. Since the axillary nerve is located within 1 cm of the inferior capsule, there is potential risk of axillary nerve injury with resultant denervation injury to the deltoid muscle when these releases are performed. However, use of the current keeled or pegged glenoid implants requires this extensive glenoid exposure for proper fitting and placement. Current glenoid replacement surgery also requires a long skin incision and extensive soft tissue stripping in order to fully expose the glenoid circumferentially, which produces a cosmetically unappealing scar. Finally, current glenoid replacement surgical techniques require advanced surgical training and expertise within the specialty of shoulder surgery, yet the majority of shoulder implants performed in the U.S. every year are performed by orthopedic surgeons who do not have advanced training in the subspecialty of shoulder surgery. Therefore, many surgeons have difficulty preparing the glenoid site for a total shoulder replacement using the current techniques.

Because there are more than 20,000 shoulder arthoplasty surgeries performed per year, many U.S. patients incur a risk of continued pain and disability, neuromuscular injuries, or failed shoulder prostheses requiring revision surgery. Thus, there remains a need for an improved glenoid implant and improved methods for performing replacement shoulder surgery.

SUMMARY OF THE INVENTION

There is provided in accordance with one aspect of the present invention, a method of treating a patient. The method comprises the steps of identifying a patient having a glenoid surface, and reaming a cavity into the glenoid surface. A glenoid implant is inserted into the cavity, such that at least a portion of a peripheral edge of the implant resides below the adjacent glenoid surface, and the portion residing below the adjacent glenoid surface is circumferentially surrounded by cortical bone of the glenoid.

The reaming a cavity step may comprise reaming a circular cavity. The inserting a glenoid implant may comprise fitting a glenoid implant having a circular portion into the cavity. The method may additionally comprise the step of securing the implant within the cavity using bone cement, a press-fit or bone screws.

The method may additionally comprise the step of stabilizing the implant within the cavity using a central peg extending from a medial surface of the implant.

The method may additionally comprise the step of accessing the glenoid via a deltapectoral approach. Alternatively, the method may comprise the step of accessing the glenoid via an anterolateral approach.

In certain implementations of the invention, the reaming a cavity step comprises reaming a cavity wholly within the boundary of the native glenoid cavity, without destroying the peripheral margin of the glenoid surface. The reaming a cavity step may be accomplished while leaving the majority of the inferior capsule intact. The reaming a cavity step may comprise reaming a cavity while leaving the peripheral cortex intact. The method may include the step of accessing the glenoid surface via an incision having a length of no more than about 9 cm.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 20A is an anterior (frontal) view of the humeral implant of the invention.

FIG. 20B is a lateral view of the humeral implant of the invention.

FIG. 20C is an anterior (frontal) view of the humeral implant of the invention with a collar.

FIG. 20D is a lateral view of the humeral implant of the invention with a collar.

DETAILED DESCRIPTION

Figure 1C:
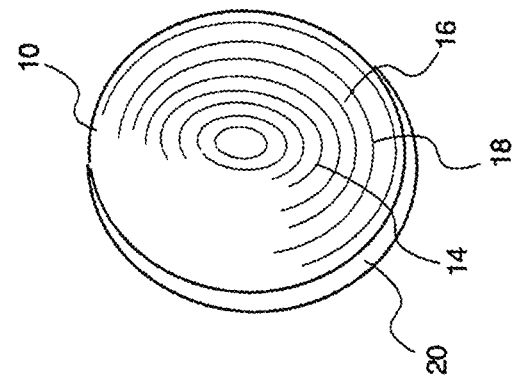
FIG. 1C is a backside view of the circular glenoid implant of FIG. 1A

The invention features an inset glenoid implant prosthesis, a humeral implant prosthesis, and methods and devices for preparing the surgical site for implantation of the implant prostheses.

In one aspect, the invention features an inset glenoid shoulder implant that is implanted within the glenoid vault, thereby allowing circumferential cortical support along the rim of the prosthesis, which improves fixation strength in comparison to current glenoid implants. Another advantage of the glenoid implant is that it requires only a minimal amount of bone removal for implantation.

The glenoid implant itself includes a (1) body portion having (i) a smooth concave lateral articulating surface facing away from the scapula, which is adapted to be engaged by a convex surface of a humeral component, and (ii) an opposing surface on the medial side intended to be positioned within a cavity reamed in the glenoid. In a preferred embodiment, the glenoid implant also includes (2) a short peg on the medial side extending centrally outward along an axis from a convex or flat backside (medial) surface of the glenoid implant. In a preferred embodiment, the short peg of the glenoid implant is less than about 10 mm long, more preferably about 8 mm or less in length, even more preferably about 5 mm or less in length. Alternatively, the glenoid implant has multiple pegs, each of which can be the same length or different lengths, e.g., less than about 8 mm or less in length, more preferably about 5 mm or less in length. In another embodiment, at least one of the pegs is between about 5 mm and about 8 mm in length and the remaining pegs are less than about 8 mm in length.

In another preferred embodiment, the body portion extends to an edge having a circular configuration while, in a second embodiment, the body portion has an edge defining a non-circular configuration, such as an oval, an elongated configuration, or a configuration which may be characterized as rectangular with slightly rounded ends. In another preferred embodiment, the glenoid implant is implanted in a prepared cavity of the glenoid which conforms generally to the backside (medial) surface only and sits inset slightly within the glenoid vault. In another preferred embodiment, the glenoid implant is implanted in a prepared cavity of the glenoid which conforms generally to the single short peg or multiple short pegs, if present, and the backside (medial) surface of the glenoid implant.

In another preferred embodiment, the glenoid implant of the invention is manufactured using polyethylene, metal, or ceramic, or combinations thereof, e.g., a combination of metal and polyethylene or ceramic and polyethylene.

In another preferred embodiment, the glenoid implant of the invention is secured to the glenoid using cement fixation or press fit technique. In yet another preferred embodiment, the glenoid implant is further secured to the glenoid using screws, e.g., in press fit designs.

In another preferred embodiment, the glenoid implant can be customized during the surgical procedure, as is required based on the condition of the patient. In another embodiment, the glenoid implant is sterilized prior to implantation. In yet another embodiment, the glenoid implant is provided in sterile packaging.

In the method of implanting the glenoid component, the first step after exposing the glenoid cavity is to determine the appropriate size of component to be used. This is done by placing a series of circular sizers having varying diameters over the glenoid cavity to determine the proper diameter to which the scapula should be reamed at the surface defining the glenoid cavity and the proper size of glenoid component. Using a combined sizer/guide having a central hole and passageway formed therein to determine the correct location and attitude, a hole is drilled a few millimeters into the scapula through the glenoid surface using a combined guide wire/drill. The guide wire/drill is calibrated in order to readily determine the depth of drilling and is attached to a chuck if a power drill is used or a T-handle or the like if the drilling is manual. The guide wire/drill should be drilled into the scapula substantially perpendicular to the anatomic axis of the glenoid surface. Thereafter, the combined sizer/guide is removed and a reamer is positioned to ream the scapula to the proper shape and depth forming a cavity having a circular cross-sectional configuration for a circular implant or an oval configuration for an oval implant in a plane normal to the axis defined by the guide wire.

In another aspect of the invention, the glenoid implant can be used in patients with deficient glenoid bone due to fracture or severe arthritis. In preferred embodiments, the glenoid implant has none, one, two, or three or more short backside pegs that do not extend beyond about 10 mm outwardly from the backside (medial) surface of the glenoid implant. In a preferred embodiment, the peg or pegs do not extend beyond about 8 mm from the backside (medial) surface of the glenoid implant. Because the glenoid implant lacks a long backside extension, it can be safely placed inside a glenoid vault with minimal depth. This minimizes the risk of fracturing the body of the scapula or injuring the suprascapular nerve or rotator cuff.

Another aspect of the invention features a humeral implant for use in a total shoulder replacement procedure. The humeral implant of the present invention is less than 70 mm in length, preferably about 60 mm in length, and is less than 40 mm wide anterior to posterior (preferably 20 to 30 mm wide). In an embodiment, the humeral implant includes a collar, which prevents the humeral implant from embedding too deeply in the humerus. In other embodiment, the humeral implant includes a flange (fin), which provides fixation of the humeral implant in the medial to lateral plane and rotational control. Alternatively, the humeral implant can contain 3 flanges (fins) with 1 lateral, 1 anterior, and 1 posterior. The stem of the humeral implant defines a longitudinal axis and the planar surface extends from between about 45° to about 60° to the axis of the stem. The proximal end of the stem includes a bore that extends downward from the planar surface and is adapted to be engaged by an artificial humeral head by means of a morse taper. In other embodiments, the humeral implant is fixed using a bone cement, such as polymethylmethacrylate (PMMA) or a compatible fixation material, or it is press-fit without bone cement. The humeral implant can be customized during the surgical procedure, as is required based on the condition of the patient. In another embodiment, the humeral implant is sterilized prior to implantation. In another embodiment, the humeral implant is provided in sterile packaging. In another preferred embodiment, the humeral implant of the invention is manufactured using polyethylene, metal, or ceramic, or combinations thereof, e.g., a combination of metal and polyethylene or ceramic and polyethylene.

Another aspect of the invention features a cutting jig for preparing a humerus for replacement by a humeral implant. The humeral head cutting jig is a simple, low profile humeral cutting jig that can be a fill circle or part thereof. The cutting jig is placed along the anatomic neck of the humerus in the appropriate version (angle of the cut) as determined by the surgeon. The cutting jig can be secured along the anatomic neck of the proximal humerus using K-wires, pins, or screws and is removed after completion of humeral head resection. In an embodiment, the cutting jig includes a handle portion.

Another aspect of the invention features a method for providing a shoulder implant which can be performed through a minimal incision technique ("mini-incision"). Instead of an extensive deltopectoral approach involving extensive soft tissue stripping, capsular releases, and circumferential glenoid exposure, this inset implant can be performed through a more limited mini-incision technique. A mini-deltopectoral incision is utilized. The skin incision is shorter, and the pectoralis tendon is left intact. The majority of the inferior capsule is also left intact. In a preferred embodiment, the glenoid labrum can be left intact if this is preferred by the surgeon. The central portion of the glenoid bone is then reamed while leaving the peripheral cortex intact. There are three major consequences of this mini-incision technique:

1—Shortening the length of the incision and exposure provides a more cosmetic incision for the patient.

2—Avoiding an extensive inferior capule incision increases the safety of the procedure by reducing the risk of injury to the axillary nerve.

3—Providing an implant that can be placed in the glenoid without extensive, circumferential glenoid exposure would allow general orthopedists to perform a shoulder replacement with less difficulty and potentially fewer complications.

The present invention is also directed to a method for implanting such glenoid implant for precise placement in the scapula and precise drilling and reaming of the scapula. The method is performed using a specialized power drill having a 90 degree drilling attachment and a short drill bit incorporated into the attachment, which is used to drill a central hole in the glenoid surface. The bone is then reamed with a reamer bit attached to the drill.

Another aspect of the invention features a slim design power drill for preparing a glenoid for implantation of a glenoid implant, in which the power drill includes a right angle drilling attachment having an extension rod with a length of at least 10 cm, more preferably at least 12, 15, or 18 cm long, the end of which is includes a collet or chuck that is positioned at a 90° angle relative to the extension rod and which is adapted to receive a short drill bit; the power drill being prepared for use in the surgical field by sterilization. In a preferred embodiment, the drill and accessories are sterilized and provided in a sterile container. In other preferred embodiments, the drill bit is 10 mm long, more preferably 12, 14, 16, 18, or 20 mm long, and most preferably 25, 35, 45, 55, 65, or 75 mm long. In other preferred embodiments, the drill bit has the following diameters: 1.5 mm, 2.5 mm, 3.0 mm, 3.2 mm, 4.0 mm, 4.5 mm, 5.0 mm, 5.5 mm, 6.0 mm, 6.5 mm, 7.0 mm, 8.0 mm, 9.0 mm, or 10.0 mm. The power drill is designed to allow drilling in spaces as tight as 50 mm. In other preferred embodiments, the overall length of the right angle drilling attachment is 18 cm, more preferably 20 cm, most preferably 22 cm. The head width and extension rod diameter are preferably less than 25 mm, more preferably less than 22 mm, and most preferably less than 20 mm. The head length is preferably less than 30 mm, more preferably less than 28 mm, and most preferably less than 25 mm. In other preferred embodiments, the right angle drilling attachment is designed to be attached to any power drill, the use of which is acceptable in a surgical field, and is designed to be lightweight, e.g., less than about 200 grams, more preferably less than about 180 grams, and most preferably less than about 150 grams. The power drill can be powered using a battery supply (cordless) or it can be powered using an electrical cord powered from a standard electrical outlet. See, e.g., U.S. Pat. No. 6,037,724, incorporated herein by reference.

I have used aircraft plane drill (sioux 90 degree air angled drill; part nos. 1am5551, 775a, and a131oah; www.planetools.com) for preparing a glenoid vault for implantation of a glenoid implant, ensuring that the drill and bit were properly sterilized prior to use. Other drills are known in the art of aircraft maintenance, once properly sterilized, are also useful in the invention (see, e.g., item #00400; www.tightfittools.com).

The design of the glenoid implant of the invention provides increased implant fixation strength to glenoid bone and therefore decreases the rate of glenoid implant loosening. This implant is also designed for use in cases of deficient glenoid bone which would preclude the use of a current glenoid implant since they require adequate bone in the glenoid vault to support multiple long pegs or a keel.

The invention also features a humeral implant, which is less than 70 mm in length, preferably about 60 mm in length, and is less than 40 mm wide from anterior to posterior (preferably 20-30 mm). The humeral implant of the invention is significantly shorter and thinner (in the anterior to posterior dimension) than most current stems, which are about 70-115 mm in length and bulkier in the proximal (metaphyseal) area than distally both in the anterior to posterior dimension and medial to lateral dimension. Because the humeral implant of the invention is shorter, it can be implanted in a narrower metaphyseal area and does not require the removal of a significant amount of bone. Fixation of the present humeral implant depends upon good interference fixation in the medial-lateral plane when press fit (similar to some current total hips). The humeral implant can be fixed using a bone cement, such as polymethylmethacrylate (PMMA) or a compatible fixation material. Alternatively, the humeral implant can be press-fit.

The invention also features a minimal incision shoulder arthroplasty technique that allows replacement of the glenoid surface and humeral head with only a small incision and less extensive soft tissue stripping. The "mini-incision" procedure also leaves the pectoralis tendon and the majority of the inferior capsule intact. The glenoid labrum can also be left intact. The central portion of the glenoid bone is then reamed while leaving the peripheral cortex intact. The advantages of this "mini-incision" procedure include a shorter incision with less scarring, increased safety, and a more simple exposure of the glenoid, thus allowing general orthopedists to perform a shoulder replacement with less difficulty and potentially fewer complications.

The glenoid implant of the invention lacks a keel and multiple long pegs, which are typically present in the prior art glenoid implants. Instead, the glenoid implant of the invention optionally includes only a single short (less than about 8 mm), central backside peg which stabilizes the glenoid implant. The glenoid implant of the invention does not require a long extended keel or long pegs because the majority of the fixation strength is concentrated on the rim of the embedded implant. This obviates the need for significant backside fixation. The fixation, with either cement or press fit techniques, offers circumferential cortical bone fixation around the prosthesis. The shear stresses placed on the implant are therefore supported by a circumferential buttress of bone, which is more mechanically sound than an onlay prosthesis with an extended backside keel or multiple long pegs.

An object of the invention is to minimize the common complications of glenoid implant loosening and fatigue failure that exist with current glenoid implants. All previous glenoid implants sit on the surface of a reamed articular surface and utilize a keel or multiple pegs to secure the implant inside the glenoid vault (see, e.g., FIGS. 3-6). This invention features a glenoid implant (which can be polyethylene, metal, ceramic, or combinations thereof) that is not designed to be placed on the surface of the reamed glenoid articular cartilage, but rather is designed to be inset partially or fully within the glenoid vault (see FIG. 7). The implant may be press fit or cemented in the reamed slot within the glenoid bone.

Patients who can benefit from the use of the glenoid implant of the invention and the improved methods for performing a total shoulder arthoplasty include young, middle, and older patients with arthritis (typical total shoulder replacement (TSR) patients) or damage or injury to the shoulder. This new inset glenoid implant allows TSR surgery for new, previously contraindicated applications, including applications in which the patient presents with bone defects on the glenoid. The glenoid implant of the invention can also be utilized in revision surgeries.

Figure 1B:
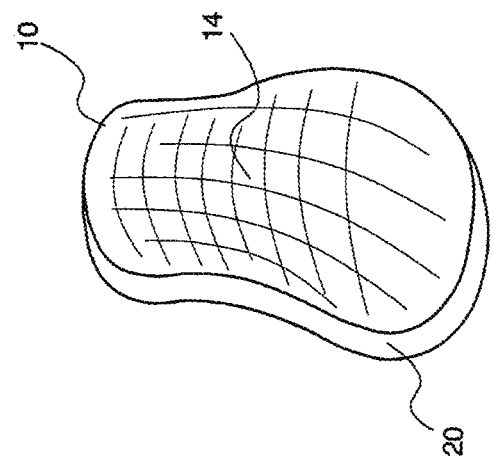
FIG. 1B is an anterior surface view of the oval glenoid implant of the invention.
Figure 1A:
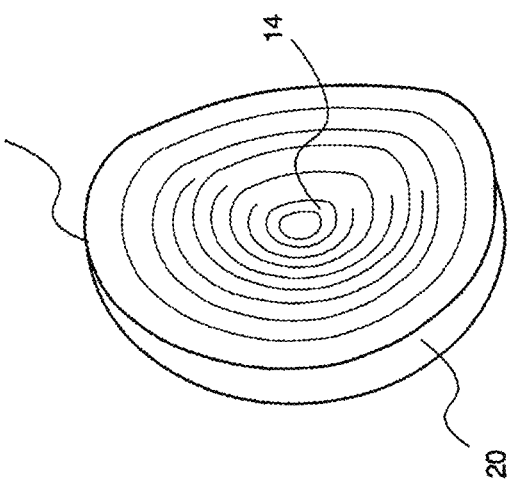
FIG. 1A is an anterior surface view of the circular glenoid implant of the invention.
Figure 15:
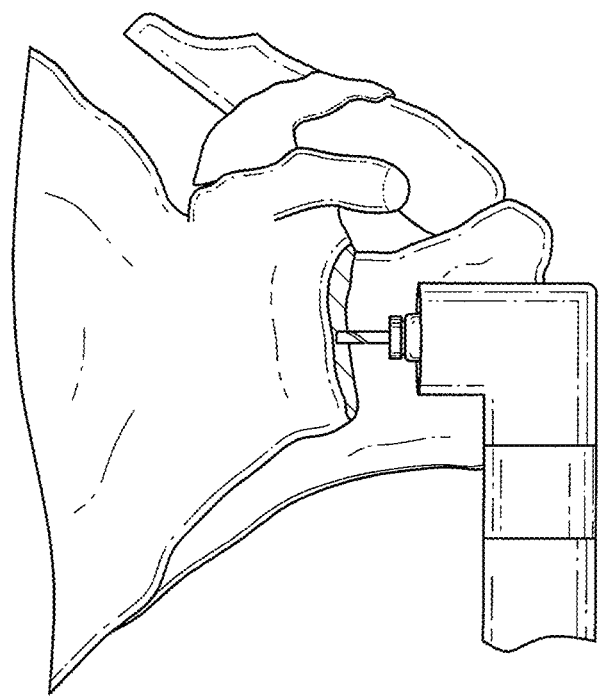
FIG. 15 is an anterior (frontal) view of the scapula showing the use of the 90° drill of the invention.
Figure 16:
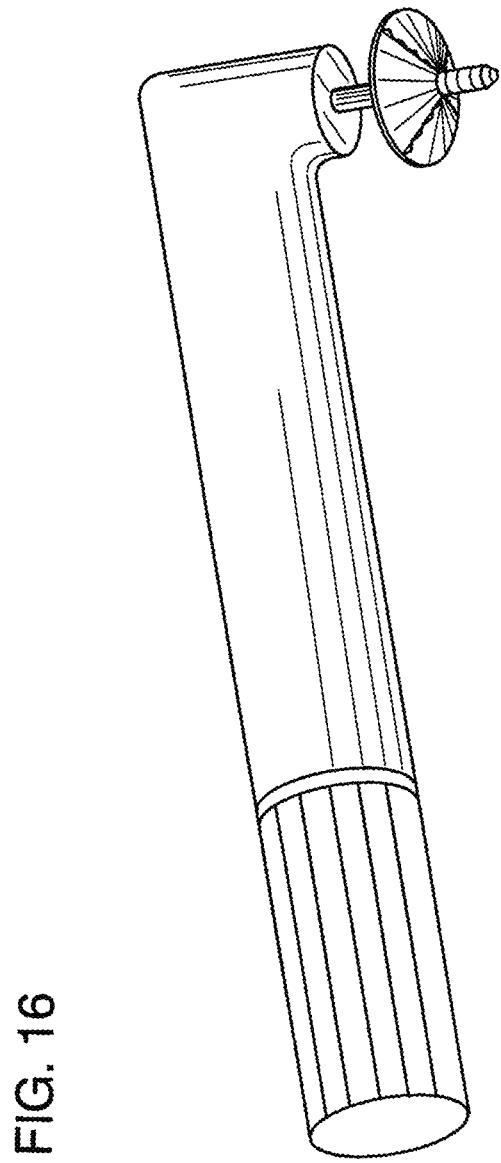
FIG. 16 is a view of the reamer of the invention.

Glenoid Implant Referring now to FIGS. 1A, 1B, and 1C, there is provided glenoid implant (10), which is intended to be implanted in the glenoid as part of a TSR arthroplasty. Glenoid implant (10) replaces the natural glenoid cavity (see G of FIG. 15) and provides a bearing surface against which the head of a humerus or humeral component may articulate. Glenoid implant (10) includes concave articulating surface (14) and convex or flat backside surface (16), which can, optionally, include roughened or textured surface (18). Glenoid implant (10) can be provided as a circular design (FIGS. 1A and 1C) or as an oblong, oval design (FIG. 1B).

Figure 2B:
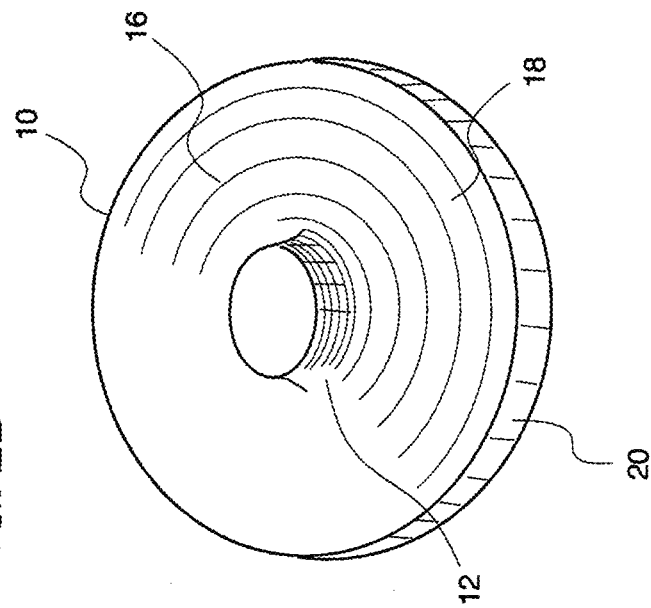
FIG. 2B is a backside view of the circular glenoid implant of FIG. 2B.
Figure 2A:
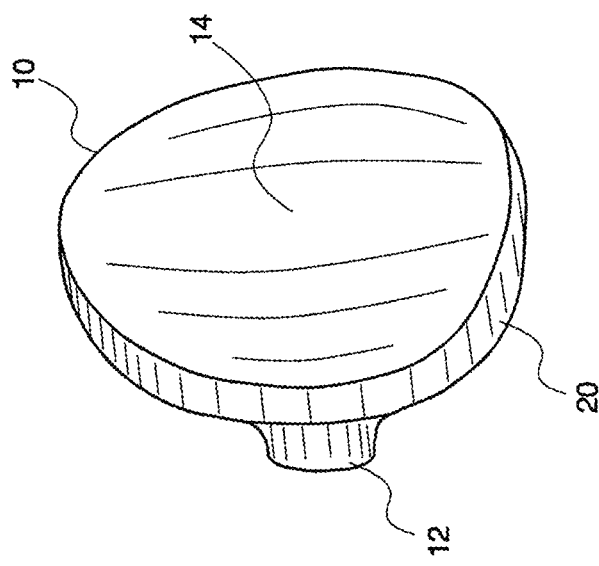
FIG. 2A is an anterior surface view of the circular glenoid implant of the invention that includes a single short backside peg.
Figure 3:
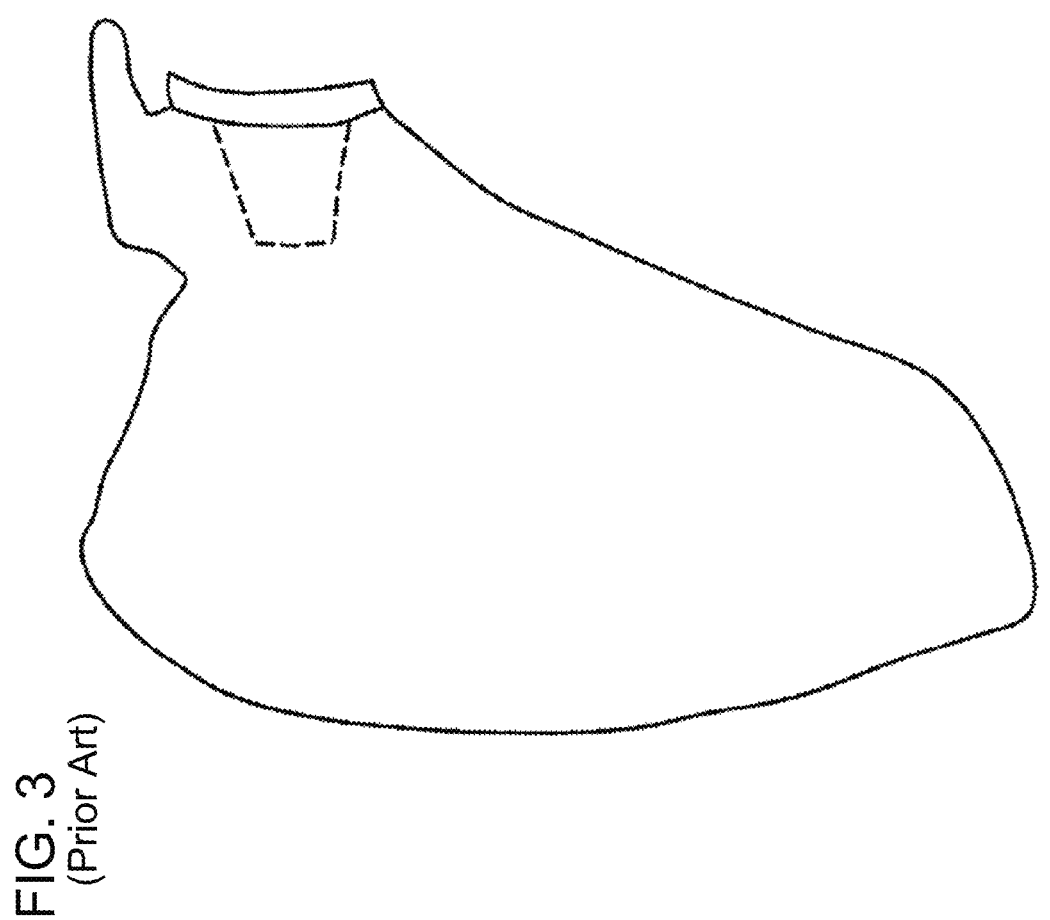
FIG. 3 is an anterior (frontal) view of a typical prior art glenoid implant with a keel design situated in the glenoid.
Figure 4:
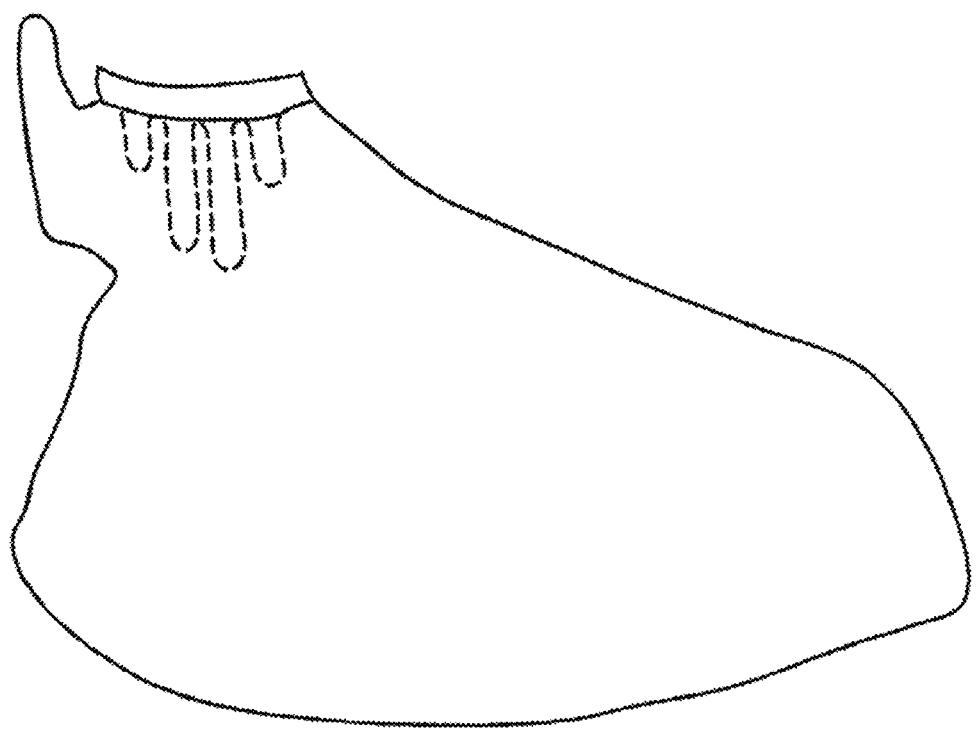
FIG. 4 is an anterior (frontal) view of a scapula containing a typical prior art glenoid implant with a multiple peg design situated in the glenoid.
Figure 5:
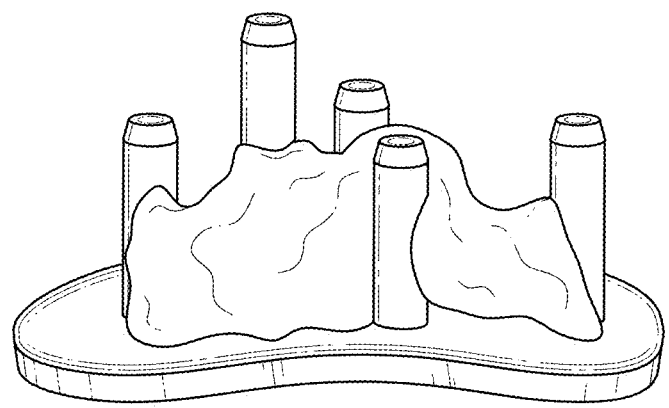
FIG. 5 is a backside view of a scapula containing a typical prior art pegged glenoid implant which was removed from a patient.
Figure 6:
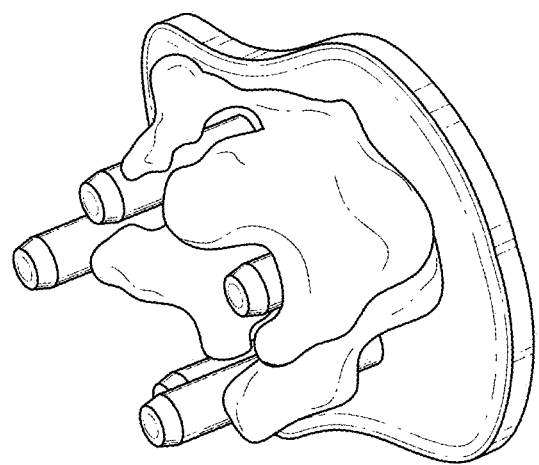
FIG. 6 is a lateral view of the prior art pegged glenoid implant of FIG. 5.

Referring now to FIGS. 2A and 2B, glenoid implant (10) can include short, backside peg (12) on the medial, convex or flat backside surface (16) of glenoid implant (10). Short, backside peg (12) is situated centrally on the medial (back) side of glenoid implant (10) and is preferably a cylindrical peg shape that extends outwardly from glenoid implant (10) away from the back of the implant (16).

Figure 12:
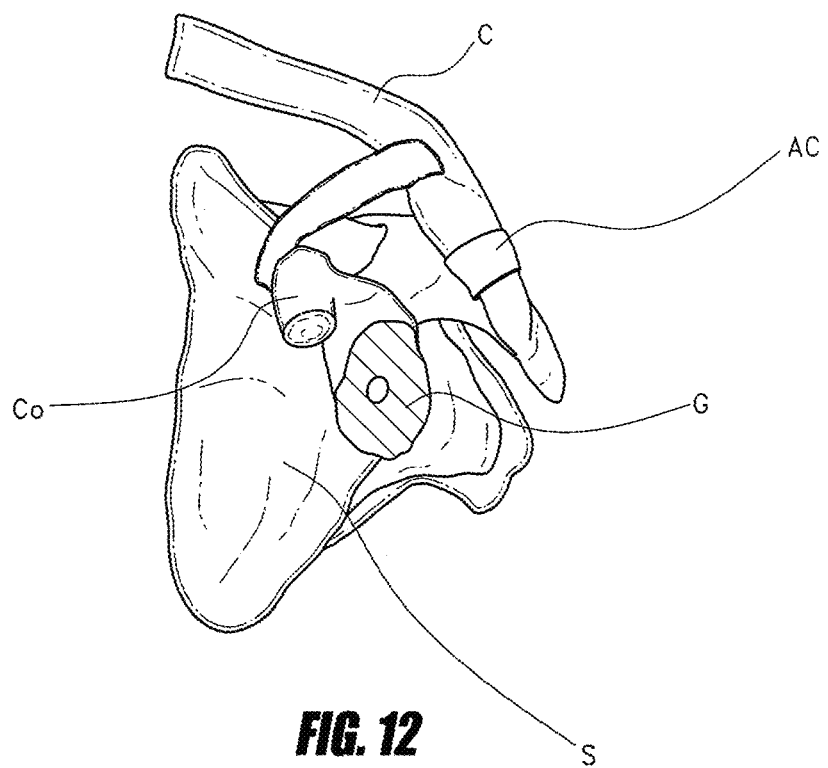
FIG. 12 is a photograph of a model depicting the glenoid (G), scapula (S), clavicle (C), Acromio-Clavicular Joint (AC), and Coracoid (Co). The glenoid is shaded to designate the placement surface for the glenoid implant of the invention.
Figure 13:
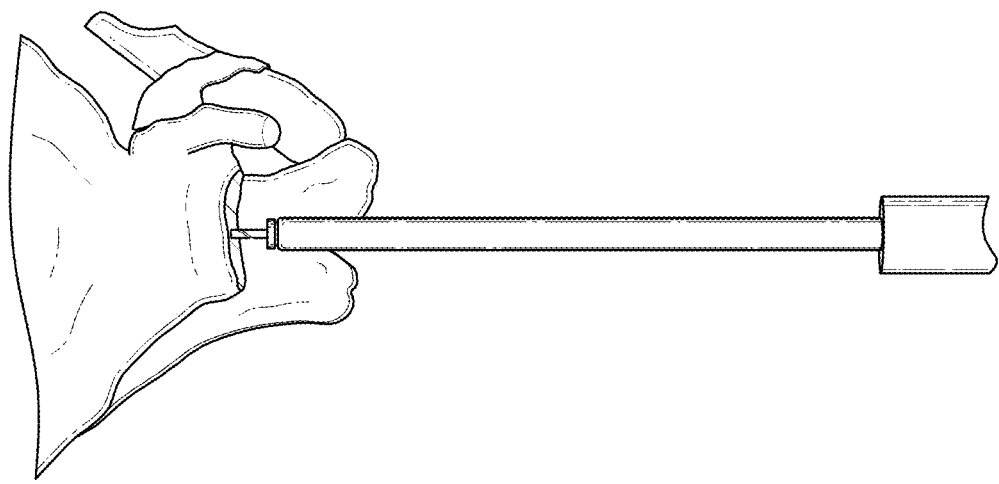
FIG. 13 is a view showing the use of a straight drill of the prior art for preparing the glenoid for implantation.
Figure 14:
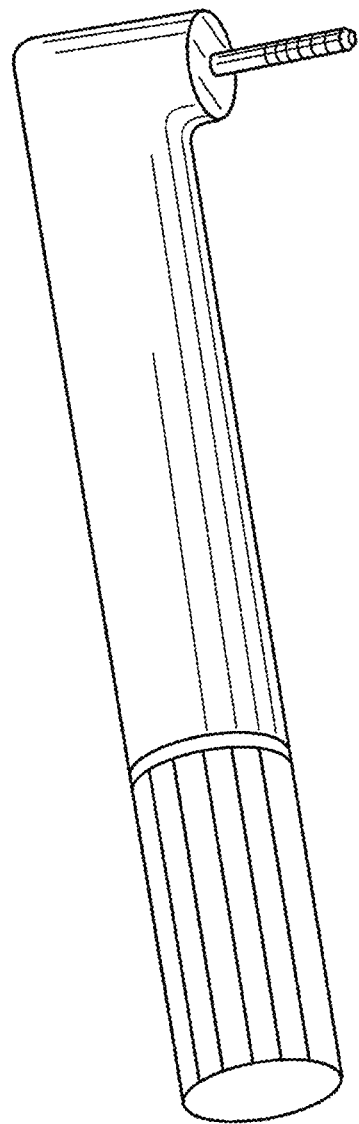
FIG. 14 is a view of the 90° drill of the invention.

Glenoid implant (10), including or excluding short, backside peg (12), is adapted to be implanted in a prepared cavity of the glenoid (see, e.g., FIG. 12), such that it is partially or fully inset to the cortical bone of the glenoid, and is retained with bone cement or using press-fit techniques. Glenoid implant (10) can be further secured to the glenoid using one or more screws.

Glenoid component (10) of the present invention includes concave lateral articulating surface (14) against which the head of a humerus or humeral component moves. Glenoid implant (10) is manufactured using a suitable material, for example, polyethylene, metal, ceramic, or combinations thereof, with lateral articulating surface (14) being smoothly contoured. The radius of curvature of the articulating glenoid surface can match the humeral head surface or it can be slightly larger than the radius of curvature of the humeral head implant.

In preferred embodiments, glenoid implant (10) has a lateral articulating surface (14) having a concave circular or oval surface encircled by circular edge (20). Circular edge (20) has a thickness in the range of about 3-6 mm, preferably about 3 mm.

The medial, back side of glenoid implant (10) is preferably roughened or textured. For example, glenoid implant (10) can include a series of elongated groves (18) in multiple locations for receiving bone cement to assist in the cement augmentation and retention of glenoid implant (10).

In preparing the glenoid to receive glenoid implant (10), the glenoid (G; see, e.g., FIG. 12) is reamed to receive all or a portion of glenoid implant (10) so that glenoid implant (10) is circumferentially surrounded by cortical bone of the glenoid (G), which aids in the stabilization and security of glenoid implant (10).

Glenoid Drill and Reamer

Referring now to FIGS. 13-16, there will be described a method for preparing a cavity in the glenoid for receiving a glenoid implant of the present invention and apparatus to be used therewith.

In preparing the cavity in the glenoid (G) to receive glenoid implant (10), the surgeon will initially determine the position of the drill site using a guide known in the art (see, e.g., U.S. Pat. Nos. 6,712,823; 6,364,910; 5,030,219; and 5,489,310; all of which are incorporated by reference).

A reamer of appropriate size is then chosen based on the size of the sizer guide previously chosen. The reamer has a symmetrical head with a plurality of cutting blades and a peripheral stop surface. The previously drilled hole is used as a center guide for the reamer. The reamer is used to create a cavity in the glenoid surface of the scapula in which the prosthetic glenoid component will be installed. After the cavity has been created, the circular or oval glenoid component is installed in the cavity, with or without the use of bone cement.

Figures 26A, 26B:
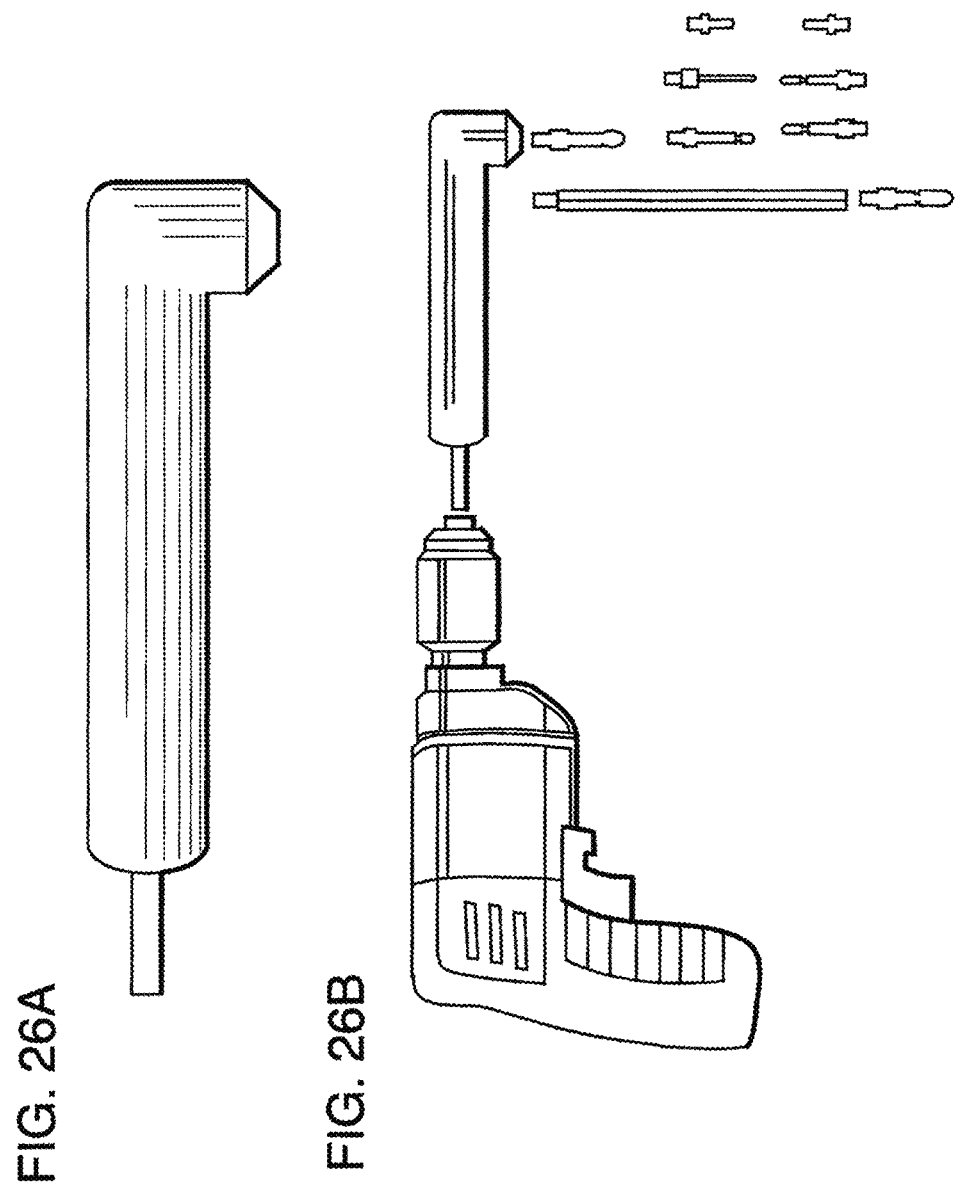
FIG. 26A is a view showing a right angle drill attachment for use in preparing a glenoid for implantation of a glenoid implant.
FIG. 26B is a view showing a drill with the right angle drill attachment and drill bits for use in preparing a glenoid for implantation of a glenoid implant.

A method for implanting glenoid implant (10) will now be described with reference to FIGS. 13-16. Initially, if a total shoulder arthroplasty is performed, a humeral implant having a head portion, discussed below, and a glenoid implant are implanted. Prior to implantation of the humeral component into the humerus, glenoid preparation begins. With the glenoid cavity (G) of the scapula (S) exposed, an alignment or pilot hole is first drilled substantially in the center of the glenoid cavity (G) using, e.g., the drill shown in FIGS. 14, 15, and 26. Once the pilot hole is drilled, the glenoid cavity (G) is reamed using a glenoid surface rasp (see bit attached to the drill depicted in FIG. 16) attached to a 90° reamer shaft with driver (see FIG. 26). The glenoid surface rasp may include a guide pin and a roughened cutting surface to create a trough for the glenoid component. The 90° angle of the shaft of the driver permits drilling in tight glenoid cavities. Thus, the procedure can be performed in a minimally invasive manner because it does not require full circumferential exposure of the glenoid, nor does it require a complete capsular release. The 90° shaft of the drill includes a quick-connect attachment which receives the quick-connect drill bit. The reamer is rotated by suitable power means or by hand to ream the glenoid cavity. Following such reaming, the reamer and the guide wire/drill are removed leaving a cavity which is wholly contained within the glenoid cavity (G).

Once the holes have been drilled and the glenoid reamed, a provisional glenoid implant may be used prior to cementing the final glenoid implant to verify hole placement, range of motion, and appropriate glenoid size, and to verify that the glenoid implant is sufficiently inset. After the proper sized glenoid implant has been selected, suitable bone cement, such as polymethylmethacrylate (PMMA) or a compatible fixation material, is placed in the reamed cavity of the glenoid vault and in the roughened outer portions and applied to the medial (back) surface of glenoid implant (10), if cement is to be used. Glenoid implant (10) can then be positioned in the prepared cavity. Glenoid implant (10) is then held in place until the cement cures to assure strong fixation of glenoid implant (10) in the scapula. The head portion of the humerus or humeral component may then engage the concave articulating surface of the glenoid implant (14).

Figure 7:
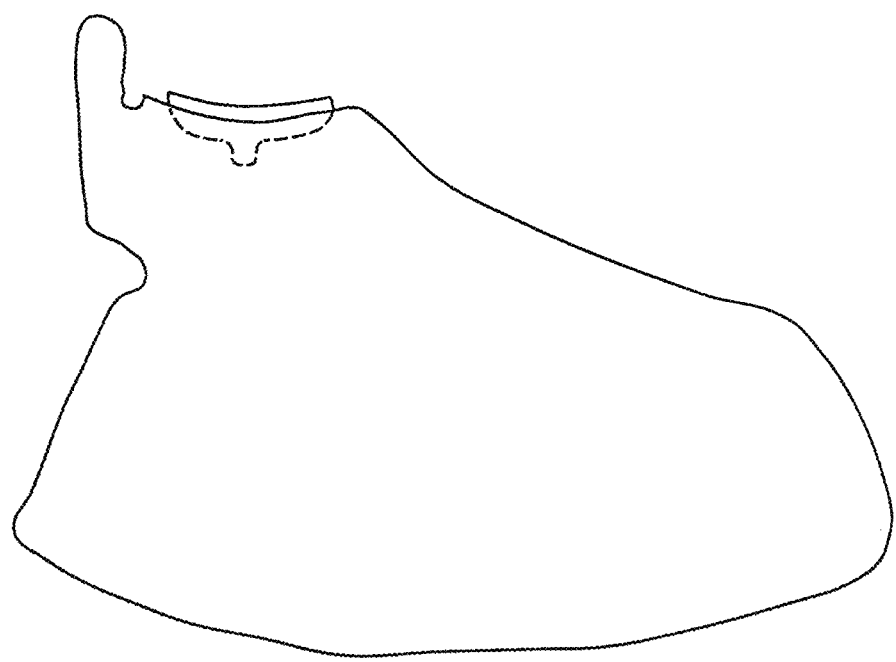
FIG. 7 is an anterior (frontal) view of a scapula containing an inset glenoid implant of the invention situated in the glenoid.
Figure 8A:
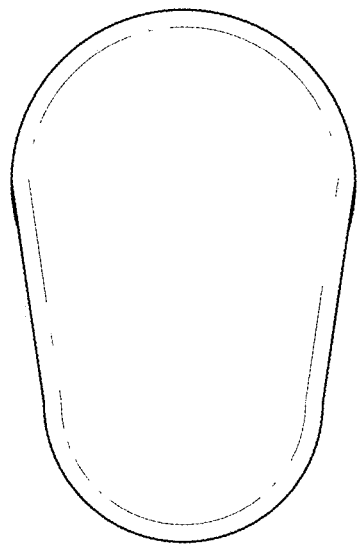
FIG. 8A is an anterior surface view of a typical prior art glenoid implant.
Figure 8B:
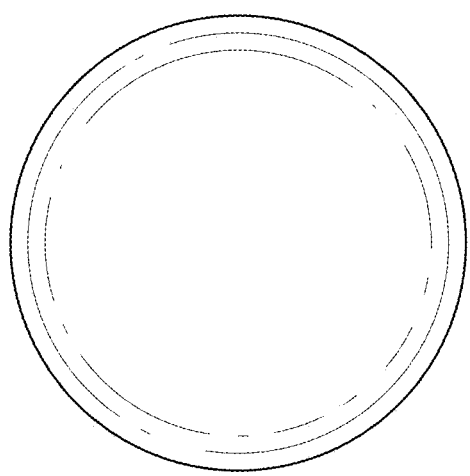
FIG. 8B is an anterior surface view of the circular glenoid of the invention.
Figure 9A:
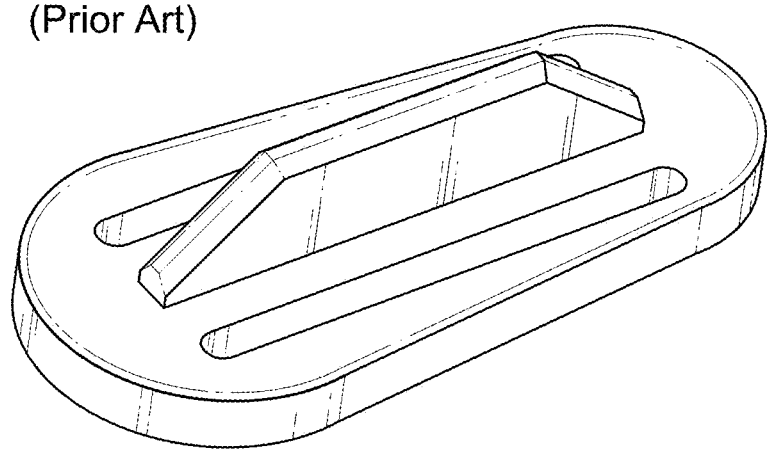
FIG. 9A is a backside view of a typical prior art keeled glenoid trial implant.
Figure 9B:
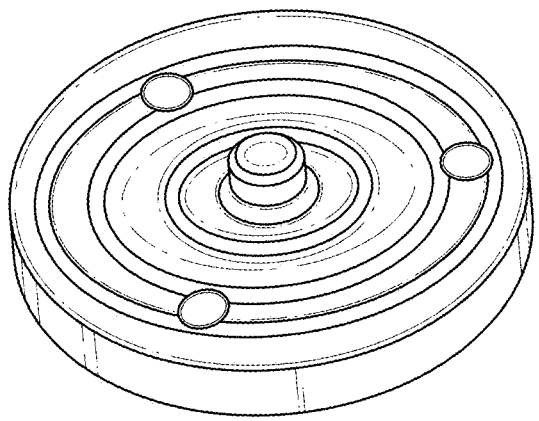
FIG. 9B is a backside view of the circular glenoid of the invention showing a short backside peg.
Figure 10A:
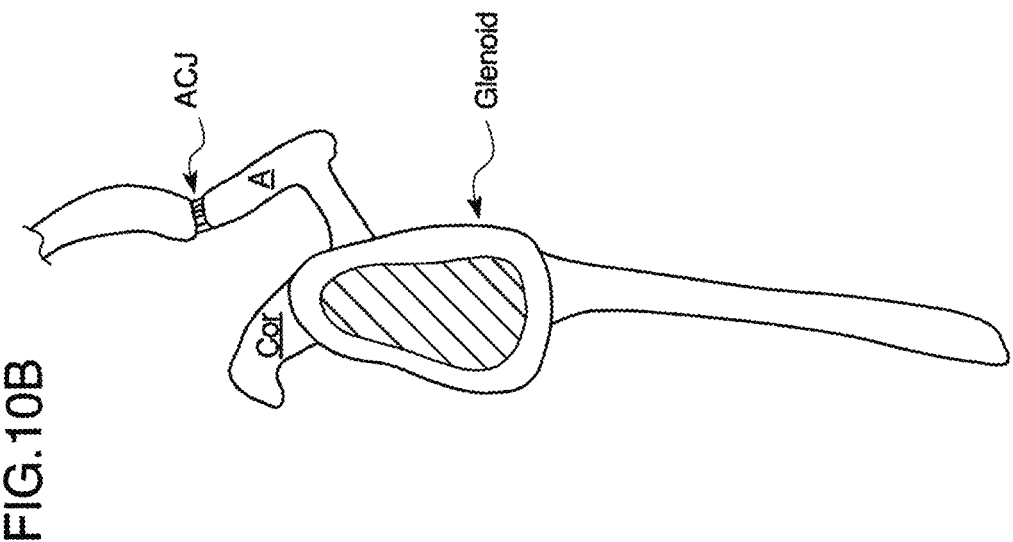
FIG. 10A is a surface view of the glenoid bone with an inset circular glenoid implant of the invention.
Figure 10B:
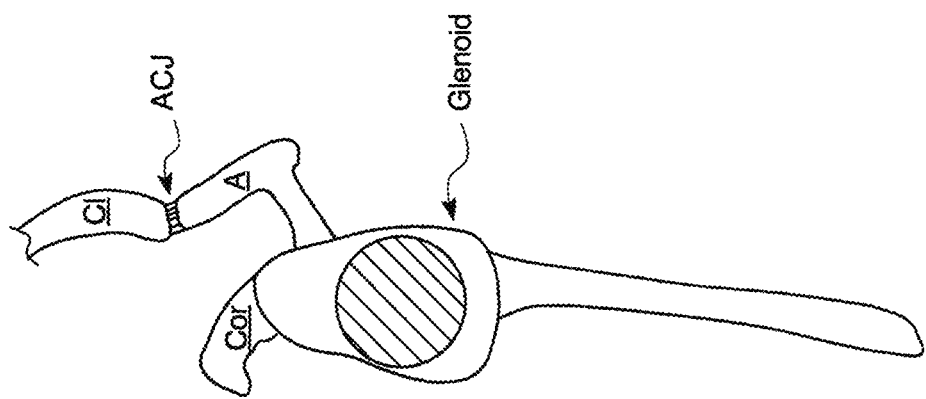
FIG. 10B is a surface view of the glenoid bone with an inset oval glenoid implant of the invention.
Figure 11:
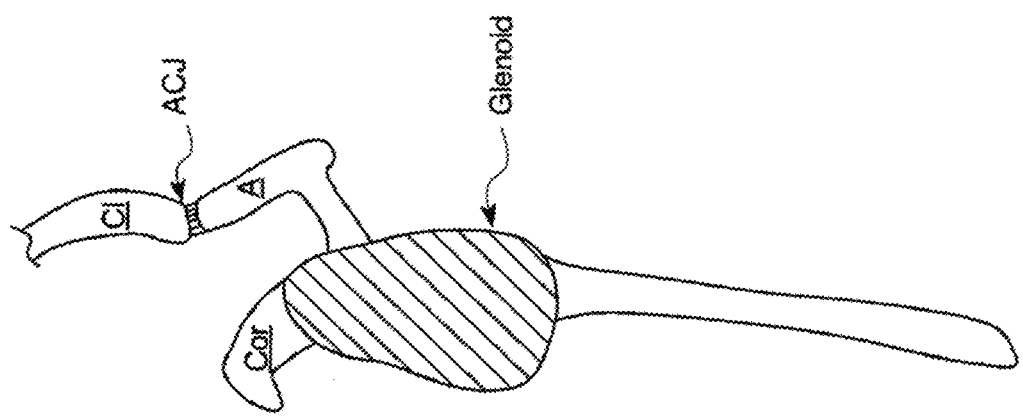
FIG. 11 is a surface view of the glenoid bone with a typical prior art onlay glenoid implant, which does not sit inset to the glenoid bone.

As can be appreciated, the reaming is contained wholly within the boundary of the glenoid cavity (G) and therefore does not destroy the peripheral margin of the glenoid surface. Additionally, as can be seen in FIG. 7, there is preferably a slight overhang of glenoid implant (10) beyond the margin of the natural glenoid cavity.

This method can be performed using a deltopectoral or anterolateral surgical approach. For most cases, a limited deltopectoral incision will be adequate to allow exposure to all involved structures. Use of glenoid implant (10) in the shoulder arthroplasty procedure allows the surgeon to use a "mini-incision technique," similar to techniques utilized for total knee surgery and total hip surgery.

The glenoid implant of the invention has already been implanted in several patients according to the patient matched implant (PMI) rules and regulations. The implants were designed specifically for patients with inadequate glenoid bone stock which could not support a typical keel or peg design.

Humeral Head Cutting Jig

Figure 17:
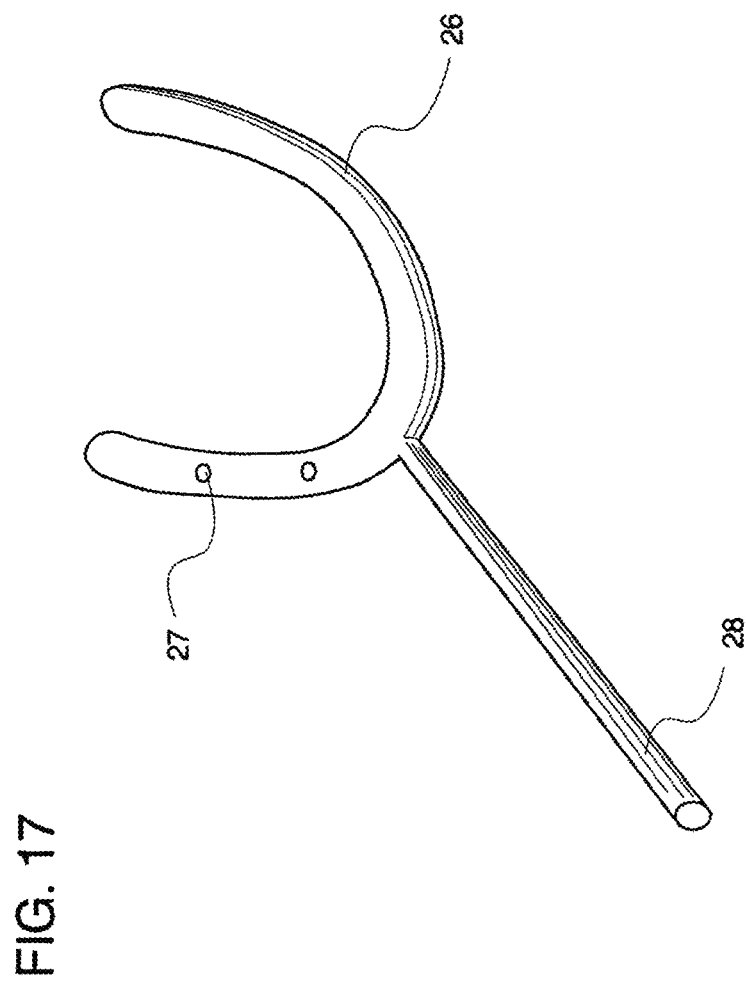
FIG. 17 is frontal view of the humeral cutting jig of the invention
Figure 18:
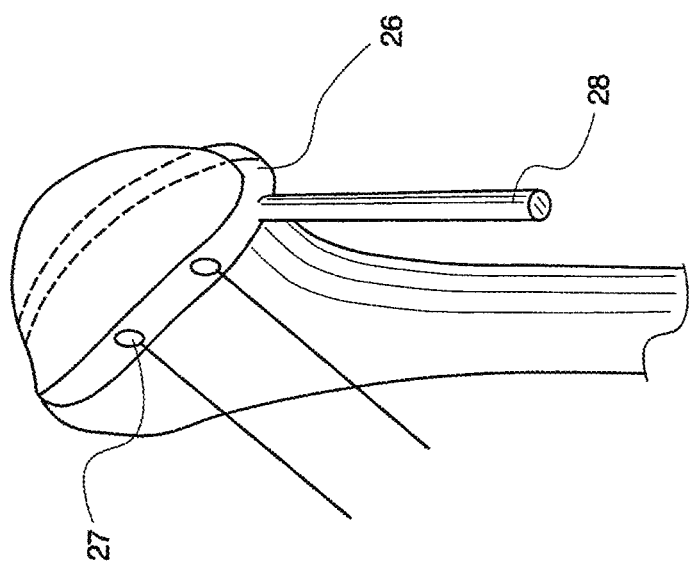
FIG. 18 is side view of the humeral cutting jig of FIG. 17 placed in position on a humerus. The cutting jig can be secured by K-wires (shown), pins, or screws.
Figure 19:
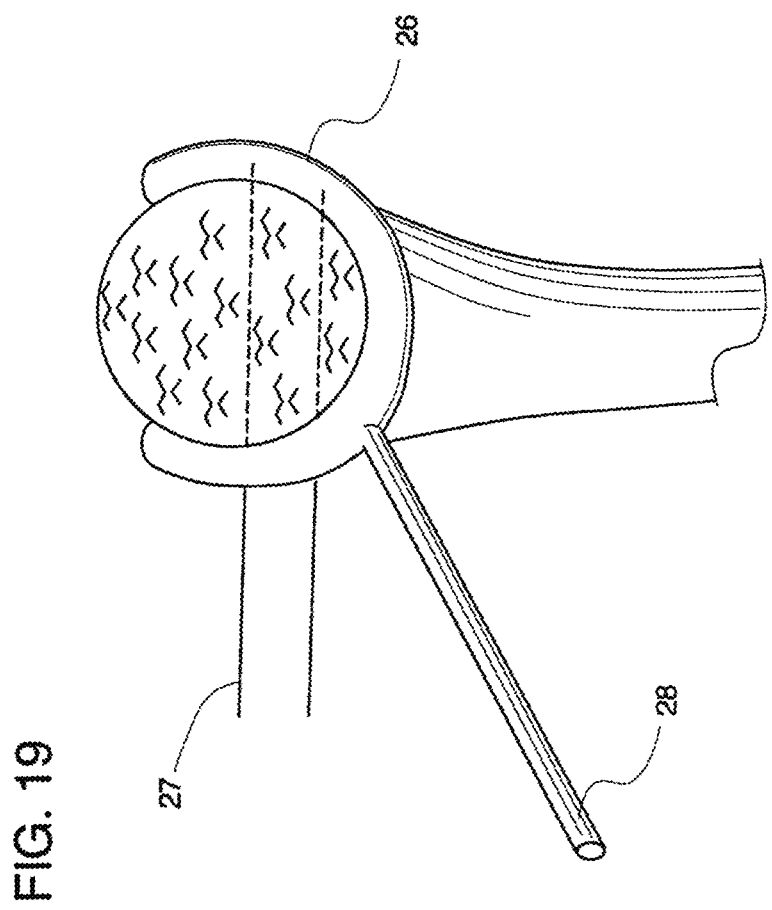
FIG. 19 is a view of the humerus and humeral cutting jig of FIG. 18 after resection of humeral head along the axis of the cutting jig.

Referring now to FIGS. 17-19, humeral head cutting jig (26) according to the present invention is a simple, low profile humeral cutting jig that can be a full circle or part thereof. Cutting jig (26) can be secured to the humeral head using K-wires, pins, or screws (27) and is removed after completion of humeral head resection. Cutting jig (26) includes handle portion (28).

The cutting jig should be placed along the anatomic neck of the humeral head. Osteophytes which obscure the junction of the humeral head and humeral shaft should be removed in order to accurately mark the level of the anatomic neck circumferentially from anterior to inferior to posterior. The cutting jig can be fixed to the humerus using wires, pins, or screws at the appropriate angle and version as determined by the surgeon. The rotator cuff should be carefully protected with retractors, and then the humeral cut is performed using an oscillating saw or osteotome along the surface of the cutting jig.

The cutting jig can be manufactured using metal.

Humeral Implant

Referring now to FIGS. 20A-D, humeral implant prosthesis (38) according to the present invention includes stem (40) having elongated portion (42) optionally including collar (44), which prevents humeral implant prosthesis (38) from embedding too deeply in the humerus. Humeral implant (38) also includes flange (fin) (46), which aids in the fixation of the stem in the humerus and prevents rotation of humeral implant in the humerus. There may be just one lateral flange (fin), or there may be two or three flanges (fins), e.g., with one lateral, one anterior, and one posterior. The stem length is preferably less than about 70 mm, and the stem width is preferably less than about 40 mm (preferably about 30 mm).

At the distal end of the stem, there is rounded portion (48) and at the proximal end of the stem is a support surface extending radially from the stem. The support surface has an upper planar surface (50) that includes bore (hole with morse taper) (52) extending inwardly from the top plane thereof, and which is adapted to be engaged by a humeral head implant with a morse taper extension. Modular humeral head implants (both concentric and eccentric) are known in the art (see, e.g., U.S. Pat. Nos. 4,865,605; 5,314,479; 5,462,563, and 5,489,309, and U.S. Patent Application Nos. 2004/0167629, 2004/0064187; each of which is incorporated herein by reference). The plane of upper planar surface (50) is preferably between about 45 degrees and about 60 degrees to the axis of the stem.

The entire stem portion, or a portion thereof, is preferably coated with a porous material for aiding in the fixation of the humeral implant in the humerus for a press fit stem. The implants made for cement fixation can have a smooth surface or a roughened, textured surface.

Humeral implant (38) can be rectangular or rounded edges, but is significantly thinner anterior to posterior than medial to lateral. It will have a morse taper for securing a standard humeral head implant.

An advantage of the humeral implant of the present invention over current humeral implant stems is that the humeral implant of the invention is significantly shorter than most current stems, which are about 70-115 mm in length. Because the humeral implant is shorter, it saves bone because of the narrow metaphyseal area required for implantation. The present humeral implant is less than 70 mm in length, preferably about 60 mm in length, and less than 40 mm anterior-posterior width (preferably about 30 mm). Fixation of the present humeral implant depends upon good interference fixation in the medial-lateral plane when press fit (similar to some current total hips). The humeral implant can be fixed using a bone cement, such as polymethylmethacrylate (PMMA) or a compatible fixation material, or it can be press-fit.

The invention will now be described by the following examples. The following examples are meant to illustrate the invention. They are not meant to limit the invention in any way.

EXAMPLES

Example 1

A 62 year old woman presented with progressive, debilitating shoulder pain from osteoarthritis, which she had experienced for approximately 15 years. She had constant pain (rated 9/10) and difficulty washing her hair, fastening her bra, lifting a cup of coffee, and performing other daily activities. The preoperative radiographs and CT scan showed severe shoulder arthritis and glenoid bone loss that would preclude the use of a keeled or pegged glenoid implant. There was concern that a hemiarthroplasty procedure (replacement of the humeral ball, which would leave the arthritic glenoid socket bare) would not relieve the patient's pain.

A total shoulder replacement using an inset glenoid implant of the invention and a standard humeral implant was performed. The smaller size and circumferential fixation of the inset glenoid implant allowed safe placement of the prosthesis within the confines of the patient's deficient glenoid cavity.

The deficient glenoid vault was not fractured and the fixation was very stable. The patient had 100% relief of pain only 1 week after surgery. Her own assessment of shoulder function 4 weeks after surgery was 56% of normal (American Shoulder and Elbow Society validated outcome score [ASES score]) was 56 compared to 16% of normal before the surgery (ASES score 16).

Figure 21:
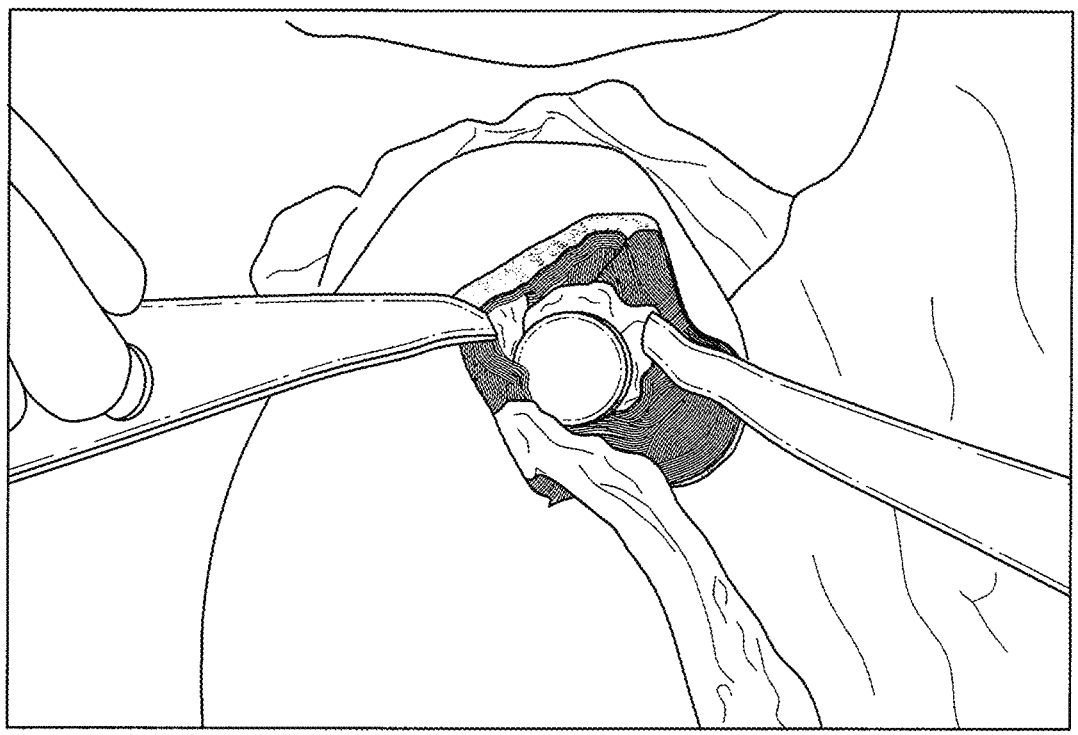
FIGS. 21, 22, and 23 are photographs showing the inset circular glenoid implant of the invention implanted in the glenoid of a patient.
Figure 22:
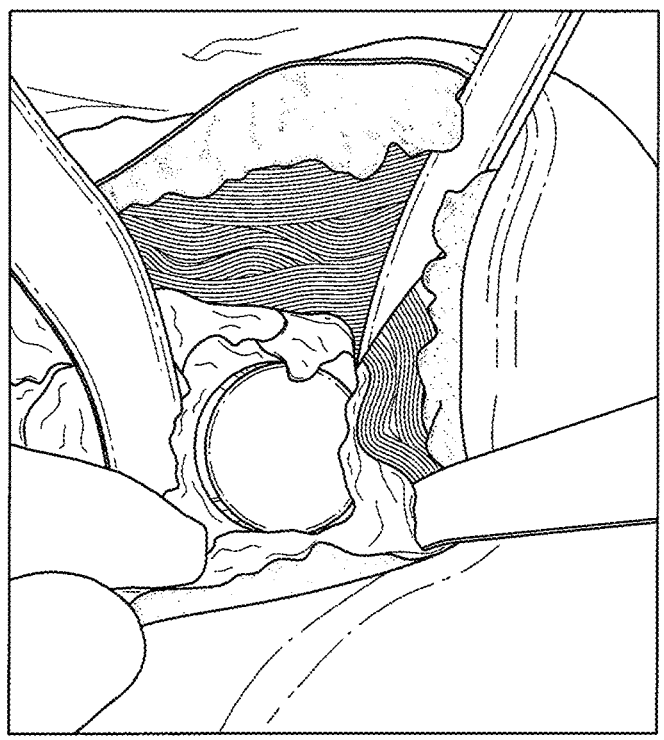
Figure 23:
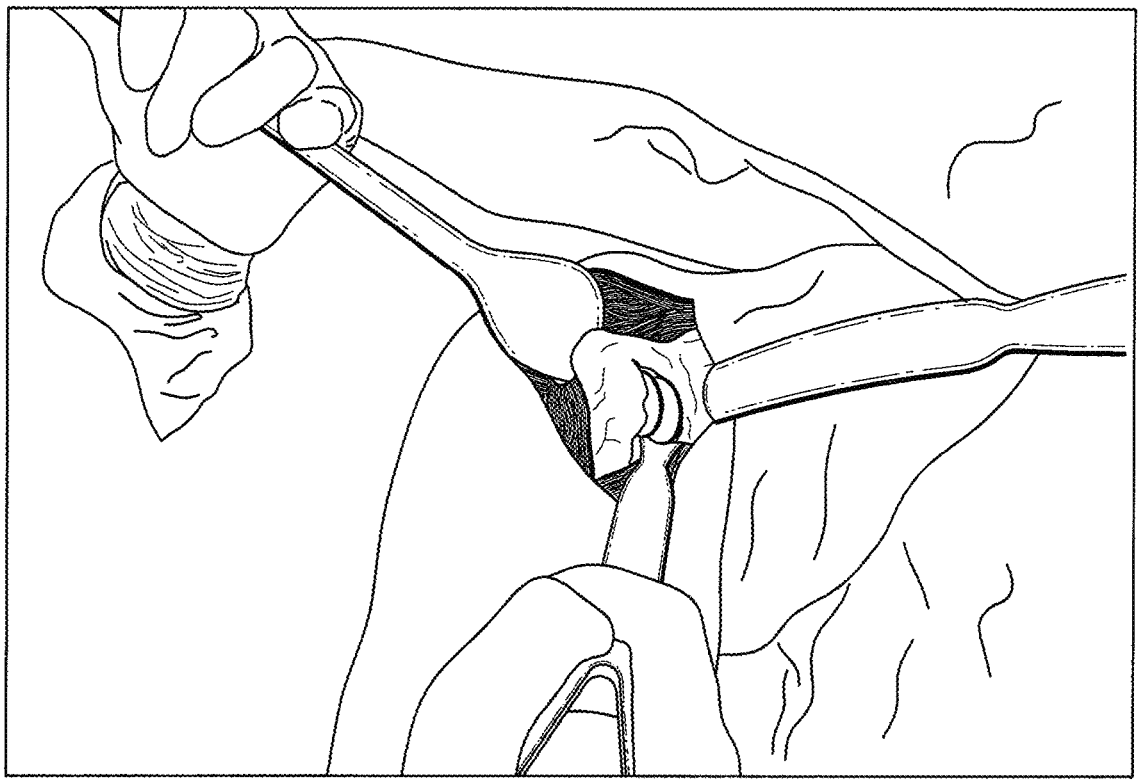
Figure 24:
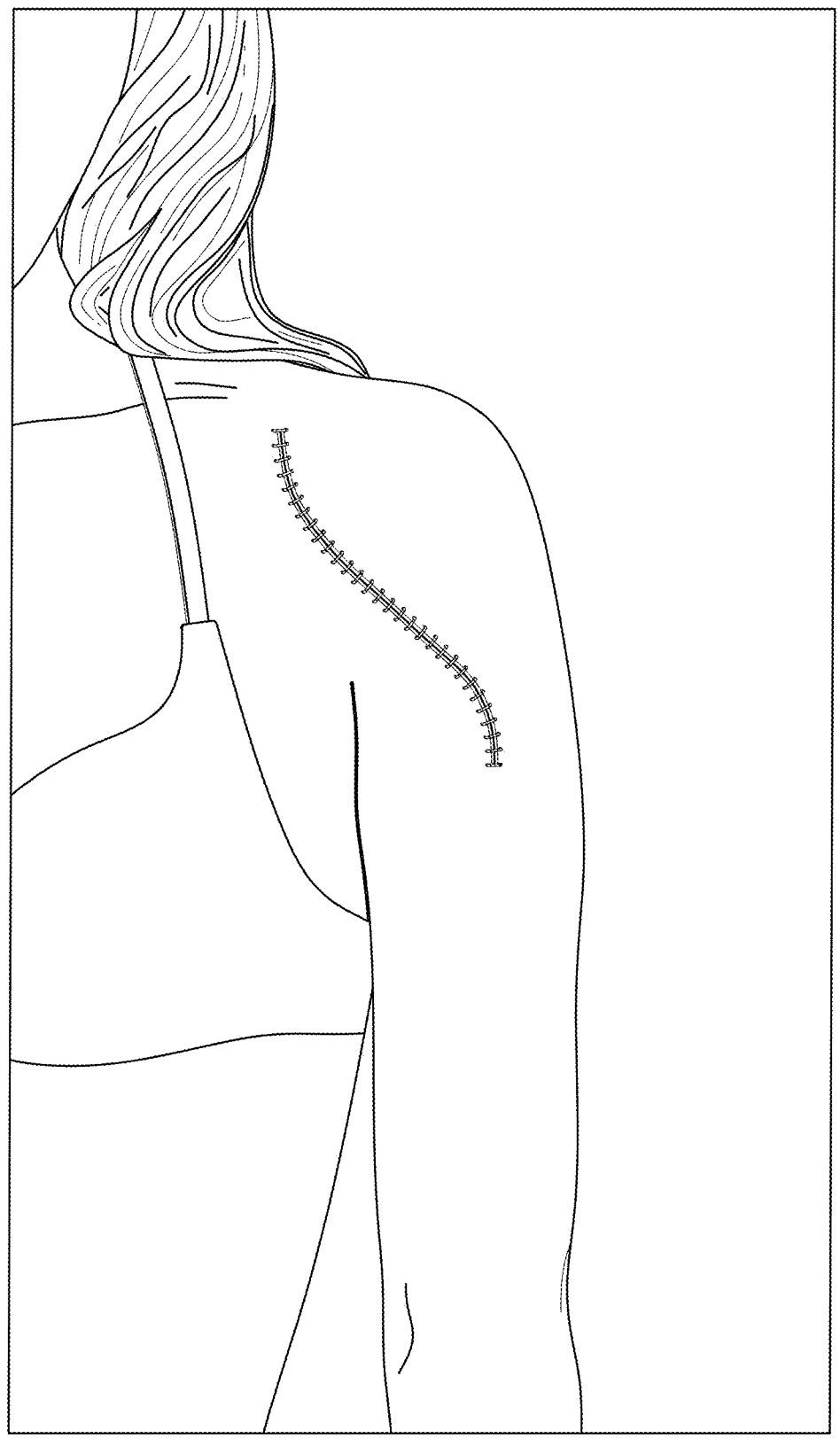
FIG. 24 is a photograph showing the 15 cm incision from a typical prior art total shoulder replacement surgery.
Figure 25:
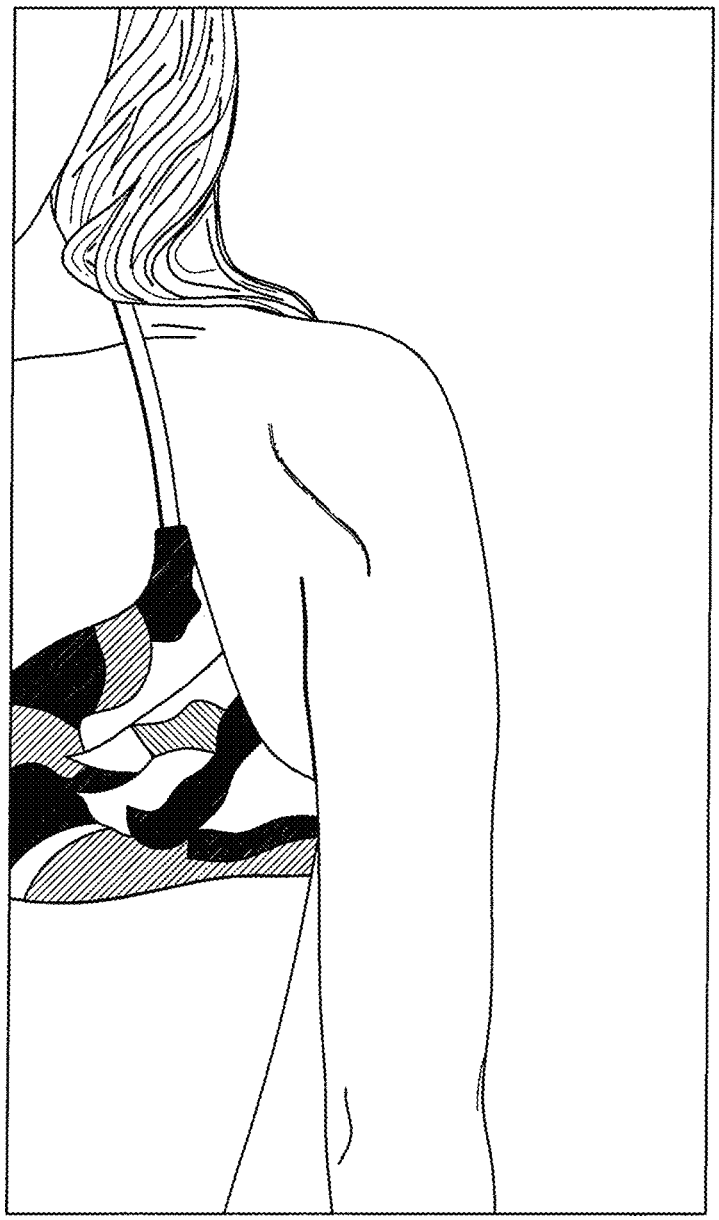
FIG. 25 is a photograph showing the 9 cm incision from the "mini-incision" total shoulder replacement surgery of the invention.

This surgery was performed through the "mini-incision total shoulder technique" described above. FIG. 25 shows the surgical incision 4 weeks post-operatively. FIG. 24, which shows a more typical total shoulder incision, clearly demonstrates the improved cosmetic appearance and reduced incision size achieved using the "mini-incision total shoulder technique" described above. FIGS. 21-23 are intraoperative pictures of the implanted inset glenoid prosthesis in this patient.

Example 2

An 81 year old woman presented with severe shoulder pain and stiffness. She had severe shoulder arthritis with medial wear causing glenoid bone loss. Her own assessment of shoulder function was 25% of normal (American Shoulder and Elbow Society validated outcome score [ASES score] was 25).

A total shoulder replacement using an inset glenoid implant prosthesis was performed. Two months after her surgery, the patient had no pain and exhibited improved function. Her own assessment of shoulder function was 70% of normal (American Shoulder and Elbow Society validated outcome score [ASES score] was 70).

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A method of treating a patient, comprising:
providing a glenoid implant having a body, the body comprising a bearing surface, a medial surface opposite the bearing surface, a circumferential peripheral edge defined between the bearing surface and the medial surface, and a radially symmetric central peg extending from said medial surface and oriented along a central axis of the implant, the circumferential peripheral edge defining a cortical-bone-contacting surface;
identifying a patient having a glenoid surface;

reaming a cavity into the glenoid surface wholly within a boundary of a native glenoid cavity of the patient without destroying the peripheral margin of the glenoid surface; and inserting the glenoid implant into the cavity, such that at least a portion of the peripheral edge of the body is inset with respect to the cavity and resides below the adjacent glenoid surface and the portion residing below the adjacent glenoid surface is circumferentially surrounded and directly supported by cortical bone of the glenoid, wherein the glenoid implant does not comprise a keel.

2. A method of treating a patient as in claim 1, wherein the peripheral edge is circular, and has a thickness of between about 3 mm and about 6 mm.

3. A method of treating a patient as in claim 1, wherein the peripheral edge of the body is fully inset with respect to the cavity.

4. A method of treating a patient as in claim 1, wherein the medial surface is roughened or textured.

5. A method of treating a patient as in claim 4, wherein the medial surface comprises a series of elongated grooves.

6. A method of treating a patient as in claim 1, wherein identifying a patient comprises identifying a patient having deficient glenoid bone.

7. A method of treating a patient as in claim 1, additionally comprising the step of stabilizing the implant within the cavity using the peg extending from the medial surface of the implant.

8. A method of treating a patient as in claim 1, additionally comprising the step of accessing the glenoid via a deltapectoral approach.

9. A method of treating a patient as in claim 1, additionally comprising the step of accessing the glenoid via an anterolateral approach.

10. A method of treating a patient as in claim 1, additionally comprising the step of accessing the glenoid via an incision no more than 9 cm in length.

11. A method of treating a patient as in claim 1, wherein the reaming a cavity step is accomplished while leaving the inferior capsule intact.

12. A method of treating a patient as in claim 1, wherein the reaming a cavity step is accomplished while leaving the peripheral cortex intact.

13. A method of treating a patient as in claim 1, wherein the reaming a cavity step is accomplished using a power drill having a 90 degree bend.

14. A method of treating a patient, comprising:

providing a glenoid implant having a body, the body comprising a bearing surface, a medial surface opposite the bearing surface, a circumferential peripheral edge defined between the bearing surface and the medial surface, and a radially symmetric central peg extending from said medial surface and oriented along a central axis of the implant, the circumferential peripheral edge defining a cortical-bone-contacting surface;

identifying a patient having a glenoid surface;

reaming a cavity into the glenoid surface wholly within a boundary of a native glenoid cavity of the patient without destroying a peripheral margin of the glenoid surface; and inserting the glenoid implant into the cavity, such that at least a portion of the peripheral edge of the body is inset with respect to the cavity and resides below the adjacent glenoid surface and the portion residing below the adjacent glenoid surface lies directly adjacent to and is circumferentially surrounded and supported by cortical bone of the glenoid, wherein the glenoid implant does not comprise a keel.

15. The method of treating a patient as in claim 14, wherein a backside surface of the glenoid implant is flat.

16. The method of treating a patient as in claim 14, wherein the central peg has a length of less than about 10 mm.

17. The method of treating a patient as in claim 14, wherein the body comprises a cylindrical peripheral edge.

18. The method of treating a patient as in claim 14, wherein the body comprises an ovoid peripheral edge.

19. The method of treating a patient as in claim 14, wherein the medial surface of the glenoid implant comprises a roughened or textured surface.

* * * * *